United States Patent
Isobe et al.

(10) Patent No.: US 9,598,657 B2
(45) Date of Patent: Mar. 21, 2017

(54) FLUORINATED POLYETHER COMPOUND, LUBRICANT, LIQUID COMPOSITION AND ARTICLE

(71) Applicant: Asahi Glass Company, Limited, Chiyoda-ku (JP)

(72) Inventors: Akira Isobe, Chiyoda-ku (JP); Kenji Ishizeki, Chiyoda-ku (JP)

(73) Assignee: Asahi Glass Company, Limited, Chiyoda-ku (JP)

( * ) Notice: Subject to any disclaimer, the term of this patent is extended or adjusted under 35 U.S.C. 154(b) by 0 days.

(21) Appl. No.: 15/002,035

(22) Filed: Jan. 20, 2016

(65) Prior Publication Data

US 2016/0137947 A1 May 19, 2016

Related U.S. Application Data

(63) Continuation of application No. PCT/JP2014/070498, filed on Aug. 4, 2014.

(30) Foreign Application Priority Data

Aug. 13, 2013 (JP) ................................. 2013-168103

(51) Int. Cl.
C10M 107/38 (2006.01)
C07C 69/708 (2006.01)
C08G 65/48 (2006.01)
C07C 43/13 (2006.01)
C07C 43/225 (2006.01)
C07F 9/6593 (2006.01)
C10M 107/48 (2006.01)

(52) U.S. Cl.
CPC .......... *C10M 107/38* (2013.01); *C07C 43/137* (2013.01); *C07C 43/225* (2013.01); *C07C 69/708* (2013.01); *C07F 9/65815* (2013.01); *C08G 65/48* (2013.01); *C10M 107/48* (2013.01); *C10M 2213/04* (2013.01); *C10M 2213/043* (2013.01); *C10M 2213/0606* (2013.01); *C10N 2220/021* (2013.01); *C10N 2230/06* (2013.01); *C10N 2240/204* (2013.01); *C10N 2270/00* (2013.01)

(58) Field of Classification Search
CPC ................ C08G 65/48; C10N 2270/00; C10N 2220/021; C10N 2240/204; C10N 2230/06; C10M 2213/0606; C10M 2213/043; C10M 2213/04
See application file for complete search history.

(56) References Cited

U.S. PATENT DOCUMENTS

| 7,956,023 B2 * | 6/2011 | Shirakawa | C10M 169/04 508/582 |
|---|---|---|---|
| 8,668,995 B2 * | 3/2014 | Shimizu | C07C 43/23 428/835.8 |
| 2005/0075517 A1 | 4/2005 | Marchionni et al. | |
| 2006/0252910 A1 | 11/2006 | Shirakawa et al. | |
| 2008/0020171 A1 | 1/2008 | Wakabayashi et al. | |
| 2010/0105584 A1 | 4/2010 | Avataneo et al. | |
| 2013/0034749 A1 | 2/2013 | Shimizu et al. | |

FOREIGN PATENT DOCUMENTS

| JP | 2001-208736 | 8/2001 |
|---|---|---|
| JP | 2005-120370 | 5/2005 |
| JP | 2009-197210 | 9/2009 |
| JP | 2010-511085 | 4/2010 |
| JP | 5028801 | 9/2012 |
| JP | 2014-80473 | 5/2014 |
| WO | WO 00/56694 | 9/2000 |
| WO | WO 2005/068534 A1 | 7/2005 |
| WO | WO 2006/009057 A1 | 1/2006 |
| WO | WO 2011/136379 A1 | 11/2011 |
| WO | WO 2013/121984 A1 | 8/2013 |
| WO | WO 2013/121985 A1 | 8/2013 |
| WO | WO 2013/121986 A1 | 8/2013 |
| WO | WO 2014/126064 A1 | 8/2014 |
| WO | WO 2014/136787 A1 | 9/2014 |

OTHER PUBLICATIONS

International Search Report issued Oct. 14, 2014 in PCT/JP2014/070498 filed Aug. 4, 2014.

\* cited by examiner

*Primary Examiner* — Cephia D Toomer
(74) *Attorney, Agent, or Firm* — Oblon, McClelland, Maier & Neustadt, L.L.P.

(57) ABSTRACT

To provide a fluorinated polyether compound capable of forming a film excellent in lubricity, a lubricant and a liquid composition, as well as an article having a film excellent in lubricity, on a substrate. A fluorinated polyether compound represented by $\{X\text{—}O\text{—}[(CF_2CF_2O)_a\text{—}(CF_2CF_2CF_2CF_2O)_b]\}_m\text{—}Y\text{—}\{[(OCF_2CF_2)_c\text{—}(OCF_2CF_2CF_2CF_2)_d]\text{—}O\text{—}Z\}_n$ is used. X is a group having a hydroxy group, a carboxy group, an ester group or an aryl group, Y is an (m+n) valent linking group, Z is a group having a haloalkyl group, each of m and n is an integer of from 1 to 10, m+n is an integer of from 2 to 20, and each of a, b, c and d is an integer of from 1 to 100.

16 Claims, No Drawings

FLUORINATED POLYETHER COMPOUND, LUBRICANT, LIQUID COMPOSITION AND ARTICLE

TECHNICAL FIELD

The present invention relates to a fluorinated polyether compound, a lubricant and liquid composition containing the fluorinated polyether compound, as well as an article having a film made of the fluorinated polyether compound.

BACKGROUND ART

A magnetic disk comprises a substrate, a magnetic recording layer formed on the surface of the substrate, a carbon protective film formed on the surface of the magnetic recording layer, and a film (hereinafter, referred to also as "the surface layer") formed by applying a lubricant to the surface of the carbon protective film for the purpose of protecting the magnetic disk and read head.

In recent years, along with an increase in the storage capacity of the hard disk drive, the space between the read head and the magnetic disk has become narrower in order to increase the recording density, and the read head and the magnetic disk are likely to get in contact. Therefore, the surface layer is required to be thinner and to be improved in lubricity.

Also, along with an increase in the reading speed of information from the magnetic disk and in the writing speed of information to the magnetic disk, rotation of the magnetic disk has become faster. Therefore, the surface layer is required to be improved in the adhesion to the carbon protective film so as not to scatter from the magnetic disk rotating at a high speed.

As lubricants to form the surface layer, for example, the following ones have been proposed.

(1) a fluorinated polyether compound having four poly(oxyperfluoroalkylene) chains bonded to a tetravalent linking group, wherein each of the chains consists solely of $(CF_2CF_2O)$ units and has a $HOCH_2CH(OH)CH_2OCH_2CF_2$— group at its terminal (Patent Document 1).

(2) a fluorinated polyether compound having at least three poly(oxyperfluoroalkylene) chains bonded to a trivalent or higher valent linking group, wherein each of the chains consists solely of $(CF_2CF_2O)$ units, and at least two chains have a $HOCH_2CF_2$— group, a $HOCH_2CH(OH)CH_2OCH_2CF_2$— group or the like at their terminals (Patent Document 2).

PRIOR ART DOCUMENTS

Patent Documents

Patent Document 1: JP-A-2009-197210
Patent Document 2: Japanese Patent No. 5,028,801

DISCLOSURE OF INVENTION

Technical Problem

However, poly(oxyperfluoroalkylene) chains consisting solely of $(CF_2CF_2O)$ units are insufficient in flexibility, and therefore, the fluorinated polyether compounds of (1) and (2) having such chains are insufficient in lubricity. Therefore, the lubricity of the surface layer formed from such fluorinated polyether compounds has become impossible to meet with the recent narrowness of the space between a magnetic disk and a read head.

An object of the present invention is to provide a fluorinated polyether compound, lubricant and liquid composition, capable of forming a film excellent in lubricity, as well as an article having a film excellent in lubricity on a substrate.

Solution to Problem

The present invention provides a fluorinated polyether compound, a lubricant, a liquid composition and an article, having the following constructions [1] to [13].

[1] A fluorinated polyether compound represented by the following formula (A):

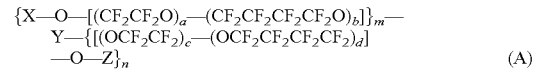

$$\{X{-}O{-}[(CF_2CF_2O)_a{-}(CF_2CF_2CF_2CF_2O)_b]\}_m{-}$$
$$Y{-}\{[(OCF_2CF_2)_c{-}(OCF_2CF_2CF_2CF_2)_d]$$
$${-}O{-}Z\}_n \qquad (A)$$

wherein X is a group having a hydroxy group, a carboxy group, an ester group or an aryl group, Y is an (m+n) valent linking group having no etheric oxygen atom at its terminals, Z is a group not having a hydroxy group, a carboxy group, an ester group or an aryl group, and having a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms, m is an integer of from 1 to 10, n is an integer from 0 to 10, m+n is an integer of from 2 to 20, and a, b, c and d are each independently an integer of from 1 to 100, provided that the linking order of a number of $(CF_2CF_2O)$ units and b number of $(CF_2CF_2CF_2CF_2O)$ units in $[(CF_2CF_2O)_a{-}(CF_2CF_2CF_2CF_2O)_b]$, and the linking order of c number of $(OCF_2CF_2)$ units and d number of $(OCF_2CF_2CF_2CF_2)$ units in $[(OCF_2CF_2)_c{-}(OCF_2CF_2CF_2CF_2)_d]$, are not limited.

[2] The fluorinated polyether compound according to [1], which has a number average molecular weight of from 500 to 50,000.

[3] The fluorinated polyether compound according to [1] or [2], wherein b/(a+b) is from 0.2 to 0.8, and d/(c+d) is from 0.2 to 0.8.

[4] The fluorinated polyether compound according to any one of [1] to [3], which has a structure wherein $(OCF_2CF_2)$ units and $(OCF_2CF_2CF_2CF_2)$ units are alternately arranged.

[5] The fluorinated polyether compound according to any one of [1] to [4], wherein X is a $HOCH_2CH(OH)CH_2OCH_2CF_2CF_2CF_2$— group or a $HOCH_2CH(OH)CH_2OCH_2CF_2$— group.

[6] A fluorinated polyether compound represented by the following formula (B):

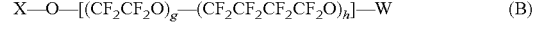

$$X{-}O{-}[(CF_2CF_2O)_g{-}(CF_2CF_2CF_2CF_2O)_h]{-}W \qquad (B)$$

wherein X is a group having a hydroxy group, a carboxy group, an ester group or an aryl group, W is a group having a hydroxy group, a carboxy group, an ester group, an aryl group, or a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms, and g and h are each independently an integer of from 1 to 200, provided that the linking order of g number of ($CF_2CF_2O$) units and h number of ($CF_2CF_2CF_2CF_2O$) units in [($CF_2CF_2O$)$_g$—($CF_2CF_2CF_2CF_2O$)$_h$] is not limited.

[7] The fluorinated polyether compound according to [6], which has a number average molecular weight of from 500 to 50,000.

[8] The fluorinated polyether compound according to [6] or [7], wherein h/(g+h) is from 0.2 to 0.8.

[9] The fluorinated polyether compound according to any one of [6] to [8], which has a structure wherein ($CF_2CF_2O$) units and ($CF_2CF_2CF_2CF_2O$) units are alternately arranged.

[10] The fluorinated polyether compound according to any one of [6] to [9], wherein X is a $HOCH_2CH(OH)CH_2OCH_2CF_2CF_2CF_2$— group or a $HOCH_2CH(OH)CH_2OCH_2CF_2$— group.

[11] A lubricant comprising the fluorinated polyether compound as defined in any one of [1] to [10].

[12] A liquid composition comprising the fluorinated polyether compound as defined in any one of [1] to [10] and a liquid medium.

[13] An article comprising a substrate and, formed thereon, a film containing the fluorinated polyether compound as defined in any one of [1] to [10].

Advantageous Effects of Invention

According to the fluorinated polyether compound, lubricant and liquid composition of the present invention, it is possible to form a film excellent in lubricity.

The article of the present invention has a film excellent in lubricity on a substrate.

DESCRIPTION OF EMBODIMENTS

The following definitions of terms apply throughout the specification and claims.

The "alkane group" means a monovalent or higher valent group having at least one hydrogen atom removed from an alkane. Here, a monovalent alkane group is an alkyl group, and a divalent alkane group is an alkylene group.

The term "perfluoro" means that all of hydrogen atoms bonded to carbon atoms are substituted by fluorine atoms.

The "fluoroalkane group" means a group having some or all of hydrogen atoms in an alkane group substituted by fluorine atoms.

The "perfluoroalkane group" means a group having all of hydrogen atoms in an alkane group substituted by fluorine atoms.

The "haloalkyl group" means a group having some or all of hydrogen atoms in an alkyl group substituted by fluorine atoms, chlorine atoms or both of them.

The "fluoroalkyl group" means a group having some or all of hydrogen atoms in an alkyl group substituted by fluorine atoms.

The "ester group" means a group represented by RC(O)O— or ROC(O)— (wherein R is a hydrocarbon group).

The "etheric oxygen atom" means an oxygen atom to form an ether bond (—O—) between carbon-carbon atoms.

The "polyether chain" means a chain-structured bivalent group having plural oxyalkylene groups (wherein some or all of hydrogen atoms in an alkylene group may be substituted by fluorine atoms, chlorine atom or both of them) linked. The "polyether chain" includes a poly(oxyalkylene) group, a poly(oxyfluoroalkylene) group, a poly(oxyperfluoroalkylene) group, etc.

[Fluorinated Polyether Compound (A)]

The first embodiment of the fluorinated polyether compound of the present invention is a fluorinated polyether compound (A) represented by the following formula (A) (hereinafter referred to also as the compound (A)).

$$\{X\text{—}O\text{—}[(CF_2CF_2O)_a\text{—}(CF_2CF_2CF_2CF_2O)_b]\}_m\text{—}Y\text{—}\{[(OCF_2CF_2)_c\text{—}(OCF_2CF_2CF_2)_d]\text{—}O\text{—}Z\}_n \quad (A)$$

(Groups Having X)

X is a group having a hydroxy group, a carboxy group, an ester group or an aryl group.

m, i.e. the number of groups having X, is an integer of from 1 to 10, preferably from 1 to 6 from the viewpoint of the solubility in a solvent, the viscosity and the superior lubricity, of the compound (A).

X may, for example, be a group (X1) represented by the following formula (X1).

$$(X^1)_i\text{-}Q^1\text{-} \quad (X1)$$

wherein $X^1$ is a hydroxy group, a carboxy group, an ester group or an aryl group, $Q^1$ is a (i+1) valent linking group (provided that it has no oxygen atom bonded to the oxygen atom adjacent on the right side, and when $X^1$ is a hydroxy group or a RC(O)O— group, it has no oxygen atom bonded thereto), and i is 1 or 2.

Group (X1) may, for example, be a group (X11) represented by the following formula (X11), a group (X12) represented by the following formula (X12), a group (X13) represented by the following formula (X13), a group (X14) represented by the following formula (X14), a group (X15) represented by the following formula (X15), or a group (X16) represented by the following formula (X16).

$$HO\text{—}(CH_2)_j Q^F\text{-} \quad (X11)$$

$$(HO)_j\text{-}Q^{11}O(CH_2)_j Q^F\text{-} \quad (X12)$$

$$HOC(O)\text{-}Q^F\text{-} \quad (X13)$$

$$R^{11}C(O)O\text{—}(CH_2)_j Q^F\text{-} \quad (X14)$$

$$R^{11}OC(O)\text{-}Q^F\text{-} \quad (X15)$$

$$\phi\text{-}Q^{12}O\text{—}(CH_2)_j Q^F\text{-} \quad (X16)$$

wherein $Q^F$ is —$CF_2$— or —$CF_2CF_2CF_2$—, $Q^{11}$ is a (i+1) valent alkane group (alkylene group or alkane-triyl group) or a (i+1) valent alkane group having an etheric oxygen atom inserted between carbon-carbon atoms, $Q^{12}$ is a single bond, —C(O)—, —NH—, an alkylene group or an alkylene group having an etheric oxygen atom inserted between carbon-carbon atoms, $R^{11}$ is a $C_{1-20}$ alkyl group, ϕ is an aryl group, i is 1 or 2, preferably 2 from the viewpoint of excellent adhesion to the carbon protective film, and j is 1 or 2, preferably 1 from the viewpoint of efficiency for preparing the compound.

As the group (X11), for example, the following groups may be mentioned.

$HOCH_2CF_2CF_2CF_2$—
$HOCH_2CF_2$—
$HOCH_2CH_2CF_2CF_2CF_2$—
$HOCH_2CH_2CF_2$—

As the group (X12), for example, the following groups may be mentioned.

$HOCH_2CH(OH)CH_2OCH_2CF_2CF_2CF_2$—
$HOCH_2CH(OH)CH_2OCH_2CF_2$—
$HOCH_2CH_2CH(OH)CH_2OCH_2CF_2CF_2CF_2$—
$HOCH_2CH_2CH(OH)CH_2OCH_2CF_2$—
$HOCH_2CH_2CH_2CH(OH)CH_2OCH_2CF_2CF_2CF_2$—

HOCH$_2$CH$_2$CH$_2$CH(OH)CH$_2$OCH$_2$CF$_2$—
HOCH$_2$CH$_2$OCH$_2$CF$_2$CF$_2$CF$_2$—
HOCH$_2$CH$_2$OCH$_2$CF$_2$—
HOCH$_2$CH$_2$CH$_2$OCH$_2$CF$_2$CF$_2$CF$_2$—
HOCH$_2$CH$_2$CH$_2$OCH$_2$CF$_2$—
HOCH$_2$CH$_2$CH$_2$CH$_2$OCH$_2$CF$_2$CF$_2$CF$_2$—
HOCH$_2$CH$_2$CH$_2$CH$_2$OCH$_2$CF$_2$—.

As the group (X13), for example, the following groups may be mentioned.
HOC(O)CF$_2$CF$_2$CF$_2$—
HOC(O)CF$_2$—.

As the group (X14), for example, the following groups may be mentioned.
R$^{11}$C(O)OCH$_2$CF$_2$CF$_2$CF$_2$—
R$^{11}$C(O)OCH$_2$CF$_2$—.

As the group (X15), for example, the following groups may be mentioned.
R$^{11}$OC(O)CF$_2$CF$_2$CF$_2$—
R$^{11}$OC(O)CF$_2$—.

As φ in the group (X16), for example, the following groups may be mentioned. Here, substituent R$^{12}$ is a hydroxy group, a halogen (provided that the halogen atom is a fluorine atom or a chlorine atom), an ester group, an alkoxy group, a hydrocarbon group, a hydrocarbon group having an etheric oxygen atom inserted between carbon-carbon atoms, a hydrocarbon group having a nitrogen atom, a haloalkyl group (provided that the halogen atom is a fluorine atom or a chlorine atom), a haloalkoxy group (provided that the halogen atom is a fluorine atom or a chlorine atom) or an aryl group, and p is an integer of 0 or more. The position of R$^{12}$ is not particularly limited, and when p is 2 or more, the plurality of R$^{12}$ may be different, and the upper limit of p is the number with which the aryl group can maintain the aromaticity. p is preferably 0 or 1.

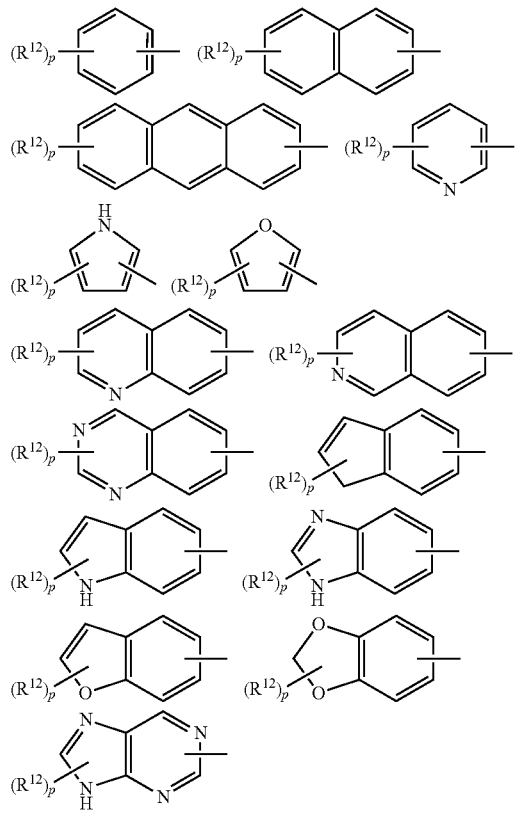

As the group (X1), from the viewpoint of excellent adhesion to the carbon protective film, group (X12) wherein i is 2, is preferred, and from the viewpoint of efficiency for production of the compound and excellent stability of the compound, the following groups are particularly preferred.

HOCH$_2$CH(OH)CH$_2$OCH$_2$CF$_2$CF$_2$CF$_2$—
HOCH$_2$CH(OH)CH$_2$OCH$_2$CF$_2$—.

(Group Y)

Y is an (m+n) valent linking group having no etheric oxygen atom at its terminals.

The valence m+n of Y is an integer of from 2 to 20, preferably an integer of from 2 to 6, whereby the compound (A) will be excellent in the solubility in a solvent, the viscosity and the lubricity, and further the compounds (A) can easily be prepared.

Y may, for example, be an (m+n) valent alkane group, an (m+n) valent alkane group having an etheric oxygen atom inserted between carbon-carbon atoms, an (m+n) valent fluoroalkane group, an (m+n) valent fluoroalkane group having an etheric oxygen atom inserted between carbon-carbon atoms, or a cyclotriphosphazene structure (P$_3$N$_3$), and an (m+n) valent perfluorinated alkane group or an (m+n) valent perfluorinated alkane group having an etheric oxygen atom inserted between carbon-carbon atoms, is preferred, whereby it is possible to lower the surface energy of the substrate by applying the compound (A), and the compound (A) will be excellent in lubricity.

As divalent Y, the following groups may be mentioned.
—CF$_2$CF$_2$—
—CH$_2$CH$_2$—

As trivalent Y, the following groups may be mentioned. Here, k is an integer of from 0 to 5.

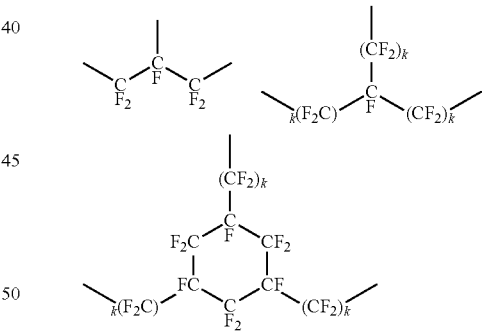

As tetravalent Y, the following groups may be mentioned.

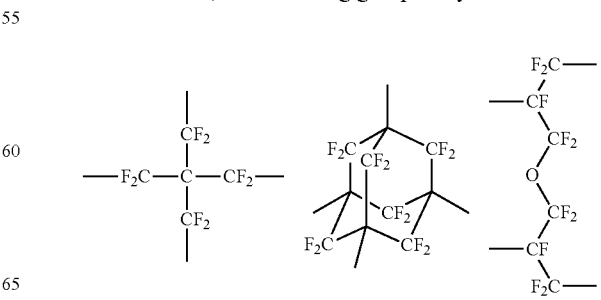

As pentavalent Y, the following group may be mentioned.

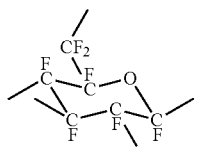

As hexavalent Y, the following groups may be mentioned.

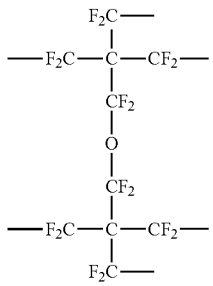 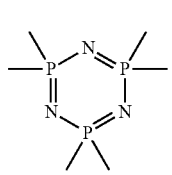

(Groups Having Z)

Z is a group not having a hydroxy group, a carboxy group, an ester group or an aryl group, and having a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms.

n, i.e. the number of groups having Z, is an integer from 0 to 10, preferably from 0 to 5, whereby the compound (A) will be excellent in solubility in a solvent, viscosity and lubricity, and further, the compound (A) can easily be prepared.

Z may, for example, be a haloalkyl group (provided that the halogen atom is a fluorine atom or a chlorine atom), or a haloalkyl group (provided that the halogen atom is a fluorine atom or a chlorine atom) having an etheric oxygen atom inserted between carbon-carbon atoms.

As Z, a group (Z1) represented by the following formula (Z1) may, for example, be mentioned.

$-Q^F(CH_2)_jOR^{21}$ (Z1)

wherein $Q^F$ is $-CF_2-$ or $-CF_2CF_2CF_2-$, $R^{21}$ is a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms, and j is 1 or 2, preferably 1, whereby the compound can easily be produced, and the compound will be excellent in stability.

As $R^{21}$ in the group (Z1), the following groups may, for example, be mentioned.

—$CH_2CF_3$
—$CH(CF_3)_2$
—$CH_2CF_2CHF_2$
—$CH_2CF_2CF_2CF_3$
—$CH_2CF_2CF_2CF_2CHF_2$
—$CH_2CH_2CF_2CF_2CF_2CF_3$
—$CH_2CH_2CF_2CF_2CF_2CF_2CF_2CF_3$
—$CH_2CH_2CF_2CF_2CF_2CF_2CF_2CF_2CF_2CF_3$
—$CH_2CCl_3$
—$CH_2CH_2Cl$ (Polyether Chain)

A polyether chain in the compound (A) is composed of $(CF_2CF_2O)$ units and $(CF_2CF_2CF_2CF_2O)$ units. A polyether chain consisting solely of $(CF_2CF_2O)$ units is insufficient in flexibility, and therefore a fluorinated polyether compound having such a polyether chain is insufficient in lubricity. By introducing $(CF_2CF_2CF_2CF_2O)$ units to such a polyether chain, the polyether chain becomes relatively soft, and a fluorinated polyether compound having such a polyether chain will be excellent in lubricity.

The polyether chain consisting of $(CF_2CF_2O)$ units and $(CF_2CF_2CF_2CF_2O)$ units preferably has a structure wherein $(CF_2CF_2O)$ units and $(CF_2CF_2CF_2CF_2O)$ units are alternately arranged, whereby the flexibility of the polyether chain is sufficient and uniformity of the flexibility in the polyether chain is excellent.

<$[(CF_2CF_2O)_a—(CF_2CF_2CF_2CF_2O)_b]$> a is an integer of from 1 to 100, and since the compound (A) will be excellent in solubility in a solvent, viscosity and lubricity, a is preferably from 1 to 50, particularly preferably from 1 to 20.

b is an integer of from 1 to 100, and since the compound (A) will be excellent in solubility in a solvent, viscosity and lubricity, b is preferably from 1 to 50, particularly preferably from 1 to 20.

b/(a+b) is preferably from 0.2 to 0.8, more preferably from 0.3 to 0.7, particularly preferably from 0.4 to 0.6, whereby the flexibility of the polyether chain will be sufficient, and the lubricity of the compound (A) will be excellent.

In $[(CF_2CF_2O)_a—(CF_2CF_2CF_2CF_2O)_b]$, the linking order of a number of $(CF_2CF_2O)$ units and b number of $(CF_2CF_2CF_2CF_2O)$ units is not limited. That is, $(CF_2CF_2O)$ units and $(CF_2CF_2CF_2CF_2O)$ units may be randomly located; $(CF_2CF_2O)$ units and $(CF_2CF_2CF_2CF_2O)$ units may be alternately arranged; or at least one block consisting of a plurality of $(CF_2CF_2O)$ units and at least one block consisting of a plurality of $(CF_2CF_2CF_2CF_2O)$ units may be linked. Since flexibility of the polyether chain will be sufficient, and uniformity of the flexibility in the chain will be excellent, $[(CF_2CF_2O)_a—(CF_2CF_2CF_2CF_2O)_b]$ preferably has a structure wherein $(CF_2CF_2O)$ units and $(CF_2CF_2CF_2CF_2O)$ units are alternately arranged, and more preferably has such alternately arranged structural portions in the polyether chain in a proportion of at least 50%, further preferably at least 80%, particularly preferably at least 90%.

As $[(CF_2CF_2O)_a—(CF_2CF_2CF_2CF_2O)_b]$ wherein $(CF_2CF_2O)$ units and $(CF_2CF_2CF_2CF_2O)$ units are alternately arranged, the following polyether chain may, for example, be mentioned.

—$CF_2CF_2O(CF_2CF_2CF_2CF_2OCF_2CF_2O)_e$— wherein e is an integer of from 1 to 99, preferably from 1 to 50, particularly preferably from 1 to 20, whereby the compound (A) will be excellent in solubility in a solvent, viscosity and lubricity.

<$[(OCF_2CF_2)_c—(OCF_2CF_2CF_2CF_2)_d]$>

C is an integer from 1 to 100, and since the compound (A) will be excellent in solubility in a solvent, viscosity and lubricity, c is preferably from 1 to 50, particularly preferably from 1 to 20.

d is an integer from 1 to 100, and since the compound (A) will be excellent in solubility in a solvent, viscosity and lubricity, d is preferably from 1 to 50, particularly preferably from 1 to 20.

d/(c+d) is preferably from 0.2 to 0.8, more preferably from 0.3 to 0.7, particularly preferably from 0.4 to 0.6, whereby flexibility of the polyether chain will be sufficient, and lubricity of the compound (A) will be excellent.

In $[(OCF_2CF_2)_c—(OCF_2CF_2CF_2CF_2)_d]$, the linking order of c number of $(OCF_2CF_2)$ units and d number of $(OCF_2CF_2CF_2CF_2)$ units is not limited. That is, $(OCF_2CF_2)$ units and $(OCF_2CF_2CF_2CF_2)$ units may be randomly located; $(OCF_2CF_2)$ units and $(OCF_2CF_2CF_2CF_2)$ units may be alternately arranged; or at least one block consisting of a plurality of $(OCF_2CF_2)$ units, and at least one block consisting of a plurality of $(OCF_2CF_2CF_2CF_2)$ units, may be linked. Since flexibility of the polyether chain will be sufficient, and uniformity of the flexibility in the chain will be excellent, $[(OCF_2CF_2)_c—(OCF_2CF_2CF_2CF_2)_d]$ preferably has a structure wherein $(OCF_2CF_2)$ units and $(OCF_2CF_2CF_2CF_2)$ units are alternately arranged, and more preferably has such alternately arranged structural portions in the polyether chain in a proportion of at least 50%, further preferably at least 80%, particularly preferably at least 90%.

As $[(OCF_2CF_2)_c—(OCF_2CF_2CF_2CF_2)_d]$ wherein $(OCF_2CF_2)$ units and $(OCF_2CF_2CF_2CF_2)$ units are alternately arranged, the following ether chain may, for example, be mentioned.

—$(OCF_2CF_2OCF_2CF_2CF_2CF_2)_eOCF_2CF_2$— wherein e is an integer from 1 to 99, preferably from 1 to 50, particularly preferably from 1 to 20, whereby the compound (A) will be excellent in solubility in a solvent, viscosity and lubricity.

(—$OCF_2O$— Structure)

The compound (A) preferably has no —$OCF_2O$— structure from the following points.

A fluorinated polyether compound having a —$OCF_2O$— structure is poor in chemical stability as compared with a fluorinated polyether compound having no —$OCF_2O$— structure.

If a polyether chain has $(CF_2O)$ units, the polyether chain tends to be too flexible, and it becomes in a random coil state. Therefore, when applied to a substrate, it is partially raised to become lumps, whereby it becomes difficult to form a thin film.

(Number Average Molecular Weight)

The number average molecular weight of the compound (A) is preferably from 500 to 50,000, more preferably from 500 to 10,000, particularly preferably from 1,000 to 5,000. When the number average molecular weight of the compound (A) is at least the above lower limit value, the solubility in a solvent, the viscosity and the lubricity will be excellent. When the number average molecular weight of the compound (A) is at most the above upper limit value, it will be less likely to be volatilized during use when it is applied on a magnetic disk.

(Production Method for Fluorinated Polyether Compound (A))

As the production method for a fluorinated polyether compound (A), for example, the following methods (1) and (2) may be mentioned. However, the production method for a fluorinated polyether compound (A) is not limited thereto.

(1) A method wherein using a polyol having (m+n) hydroxy groups as the starting point, $CF_2=CFOCF_2CF_2CF_2CH_2OH$ is addition-polymerized, followed by fluorination, to form polyether chains bonded by an (m+n) valent Y, whereupon X and, if required, Z may be introduced at the terminals.

(2) A method wherein a fluorinated polyether compound having X introduced at one end of the polyether chain, and, if required, a fluorinated polyether compound having Z introduced at one end of the polyether chain, are prepared and reacted with a compound having (m+n) —$SO_2CH_3$ groups, etc.

In the following, methods (1-1) to (1-3) will be described as examples of the method (1), and methods (2-1) and (2-2) will be described as examples of the method (2).

<Method (1-1)>

A production method for a compound (A1) represented by the following formula (A1), a compound (A2) represented by the following formula (A2) and a compound (A5) represented by the following formula (A5) will be described.

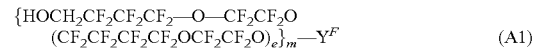

$\{HOCH_2CF_2CF_2CF_2—O—CF_2CF_2O(CF_2CF_2CF_2CF_2OCF_2CF_2O)_e\}_m—Y^F$ (A1)

$\{HOCH_2CH(OH)CH_2OCH_2CF_2CF_2CF_2—O—CF_2CF_2O(CF_2CF_2CF_2CF_2OCF_2CF_2O)_e\}_m—Y^F$ (A2)

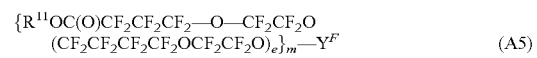

$\{R^{11}OC(O)CF_2CF_2CF_2—O—CF_2CF_2O(CF_2CF_2CF_2CF_2OCF_2CF_2O)_e\}_m—Y^F$ (A5)

wherein $Y^F$ is an (m+n) valent perfluorinated alkane group having no etheric oxygen atom at its terminals, or an (m+n) valent perfluorinated alkane group having an etheric oxygen atom inserted between carbon-carbon atoms and having no etheric oxygen atom at its terminals.

$HOCH_2CF_2CF_2CF_2$— in the compound (A1) is a group (X11), $HOCH_2CH(OH)CH_2OCH_2CF_2CF_2CF_2$— in the compound (A2) is a group (X12), and $R^{11}OC(O)CF_2CF_2CF_2$— in the compound (A5) is a group (X15).

A compound (1) represented by the following formula (1) is reduced with a reducing agent (sodium borohydride, etc.) to obtain a compound (2) represented by the following formula (2).

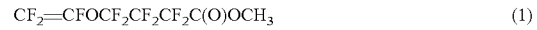

$CF_2=CFOCF_2CF_2CF_2C(O)OCH_3$ (1)

$CF_2=CFOCF_2CF_2CF_2CH_2OH$ (2)

In the presence of a basic compound (potassium carbonate, etc.) or a quaternary ammonium salt, using a compound (3) represented by the following formula (3) as a starting point, the compound (2) is addition-polymerized to obtain a compound (4) represented by the following formula (4). Here, $Y^1$ is an (m+n) valent alkane group terminated with $CH_2$ without having an etheric oxygen atom at its terminals, an (m+n) valent alkane group having an etheric oxygen atom inserted between carbon-carbon atoms, an (m+n) valent fluoroalkane group, or an (m+n) valent fluoroalkane group having an etheric oxygen atom inserted between carbon-carbon atoms.

$(HO)_m—Y^1$ (3)

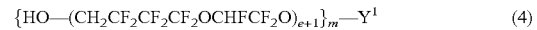

$\{HO—(CH_2CF_2CF_2CF_2OCHFCF_2O)_{e+1}\}_m—Y^1$ (4)

By an esterification reaction of the compound (4) with a compound (5) represented by the following formula (5), a compound (6) represented by the following formula (6) will be obtained. Here, $R^f$ is a perfluoroalkyl group or a perfluoroalkyl group having an etheric oxygen atom inserted between carbon-carbon atoms. Instead of the acid fluoride of the compound (5), an acid chloride, an acid bromide, an acid anhydride or the like, may be used.

$R^fC(O)F$ (5)

$\{R^fC(O)O—(CH_2CF_2CF_2CF_2OCHFCF_2O)_{e+1}\}_m—Y^1$ (6)

A compound (7) represented by the following formula (7) is obtained by substituting hydrogen atoms in the compound (6) to fluorine atoms by using a fluorine gas. Such fluorination may be carried out, for example, in accordance with the method disclosed in WO2000/56694.

$$\{R^fC(O)O-(CF_2CF_2CF_2CF_2OCF_2CF_2O)_{e+1}\}_m-Y^F \quad (7)$$

The compound (7) is reacted with a compound (8) represented by the following formula (8) to obtain a compound (A5).

$$R^{11}OH \quad (8)$$

$$\{R^{11}OC(O)CF_2CF_2CF_2-O-CF_2CF_2O\\ (CF_2CF_2CF_2CF_2OCF_2CF_2O)_e\}_m-Y^F \quad (A5)$$

The compound (A5) is reduced with a reducing agent (sodium borohydride, etc.) to obtain a compound (A1).

$$\{HOCH_2CF_2CF_2CF_2-O-CF_2CF_2O\\ (CF_2CF_2CF_2CF_2OCF_2CF_2O)_e\}_m-Y^F \quad (A1)$$

A compound (9) represented by the following formula (9) is reacted to the compound (A1) to obtain a compound (A2).

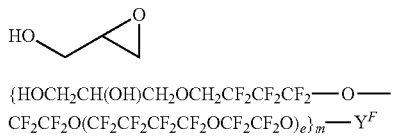

(9)

$$\{HOCH_2CH(OH)CH_2OCH_2CF_2CF_2CF_2-O-\\ CF_2CF_2O(CF_2CF_2CF_2CF_2OCF_2CF_2O)_e\}_m-Y^F \quad (A2)$$

<Method (1-2)>

A production method for a compound (A11) represented by the following formula (A11) will be described.

$$\{HOCH_2CF_2CF_2CF_2-O-CF_2CF_2O\\ (CF_2CF_2CF_2CF_2OCF_2CF_2O)_e\}_m-Y^F-\{\\ (OCF_2CF_2CF_2CF_2OCF_2CF_2)_eOCF_2CF_2-O-\\ CF_2CF_2CF_2CH_2OR^{21}\}_n \quad (A11)$$

$HOCH_2CF_2CF_2CF_2-$ is a group (X11), and
$-CF_2CF_2CF_2CH_2OR^{21}$ is a group (Z1).

A compound (A1) is obtained in the same manner as in the method (1-1).

$$\{HOCH_2CF_2CF_2CF_2-O-CF_2CF_2O\\ (CF_2CF_2CF_2CF_2OCF_2CF_2O)_e\}_{m+n}-Y^F \quad (A1)$$

In the presence of a basic compound (triethylamine, trimethylamine hydrochloride, etc.), a compound (10) represented by the following formula (10) is reacted with mesyl chloride to obtain a compound (11) represented by the following formula (11).

$$HOR^{21} \quad (10)$$

$$CH_3SO_2-OR^{21} \quad (11)$$

The compound (A1) and metallic sodium or a basic compound (sodium hydride, potassium tert-butoxide) are reacted and then further reacted with the compound (11). The obtained crude product is purified by a silica gel column by the method disclosed in Examples of JP-A-2009-197210, to obtain a compound (A11).

$$\{HOCH_2CF_2CF_2CF_2-O-CF_2CF_2O\\ (CF_2CF_2CF_2CF_2OCF_2CF_2O)_e\}_m-Y^F-\{\\ (OCF_2CF_2CF_2CF_2OCF_2CF_2)_eOCF_2CF_2-O-\\ CF_2CF_2CF_2CH_2OR^{21}\}_n \quad (A11)$$

<Method (1-3)>

A production method for a compound (A6) represented by the following formula (A6) will be described.

$$\{\phi Q^{12}OCH_2CF_2CF_2CF_2-O-CF_2CF_2O\\ (CF_2CF_2CF_2CF_2OCF_2CF_2O)_e\}_m-Y^F \quad (A6)$$

$\phi Q^{12}O(CH_2)_jQ^F-$ is a group (X16).

A compound (A1) is obtained in the same manner as in the method (1-1).

$$\{HOCH_2CF_2CF_2CF_2-O-CF_2CF_2O\\ (CF_2CF_2CF_2CF_2OCF_2CF_2O)_e\}_m-Y^F \quad (A1)$$

The compound (A1) and metallic sodium or a basic compound (sodium hydride, potassium tert-butoxide) are reacted and then further reacted with a compound (12) represented by the following formula (12) to obtain a compound (A6). Here, A is a hydroxy group, an iodine atom or a bromine atom, and in the case of the hydroxyl group, it can be used after reacted with mesyl chloride in the same manner as in the method (1-2).

$$\phi Q^{12}-A \quad (12)$$

$$\{\phi Q^{12}OCH_2CF_2CF_2CF_2-O-CF_2CF_2O\\ (CF_2CF_2CF_2CF_2OCF_2CF_2O)_e\}_m-Y^F \quad (A6)$$

<Method (2-1)>

A production method for a compound (A61) represented by the following formula (A61) and a compound (A62) represented by the following formula (A62) will be described.

$$\{\phi Q^{12}O(CH_2)_jQ^F-O-[(CF_2CF_2O)_a-\\ (CF_2CF_2CF_2CF_2O)_b]-Q^F(CH_2)_jO\}_{m+n}-Y^2 \quad (A61)$$

$$\{\phi Q^{12}O(CH_2)_jQ^F-O-[(CF_2CF_2O)_a-\\ (CF_2CF_2CF_2CF_2O)_b]-Q^F(CH_2)_jO\}_m-Y^2-\{O\\ (CH_2)_jQ^F-[(OCF_2CF_2)_c-(OCF_2CF_2CF_2\\ CF_2)_d]-O-Q^F(CH_2)_jOR^{21}\}_n \quad (A62)$$

Here, $Y^2$ is an (m+n) valent alkane group terminated with $CH_2$ without having an etheric oxygen atom at its terminals, an (m+n) valent alkane group having an etheric oxygen atom inserted between carbon-carbon atoms, an (m+n) valent fluoroalkane group, or an (m+n) valent fluoroalkane group having an etheric oxygen atom inserted between carbon-carbon atoms.

$\{-Q^F(CH_2)_jO\}_m-Y^2-\{O(CH_2)_jQ^F-\}_n$ corresponds to Y,
$\phi Q^{12}O(CH_2)_jQ^F-$ is a group (X16), and
$-Q^F(CH_2)_jOR^{21}$ is a group (Z1).

A compound (13) represented by the following formula (13) and a compound (14) represented by the following formula (14) are prepared. The production methods for the compound (13) and the compound (14) will be described later in the method (3).

$$HO(CH_2)_jQ^F-O-[(CF_2CF_2O)_a-(CF_2CF_2CF_2\\ CF_2O)_b]-Q^F(CH_2)_jOH \quad (13)$$

$$HO(CH_2)_jQ^F-[(OCF_2CF_2)_c-(OCF_2CF_2CF_2CF_2)_d]-\\ OQ^F(CH_2)_jOH \quad (14)$$

In the same manner as in the method (1-3), the compound (13) and metallic sodium or a basic compound (sodium hydride, potassium tert-butoxide) are reacted and then further reacted with a compound (12). The obtained crude product is purified by a silica gel column by the method disclosed in Examples of JP-A-2009-197210, to obtain a compound (15) represented by the following formula (15).

$$\phi Q^{12}-A \quad (12)$$

$$\phi Q^{12}O(CH_2)_jQ^F-O-[(CF_2CF_2O)_a-\\ (CF_2CF_2CF_2CF_2O)_b]-Q^F(CH_2)_jOH \quad (15)$$

In the same manner as in the method (1-2), the compound (14) and metallic sodium or a basic compound (sodium hydride, potassium tert-butoxide) are reacted and then further reacted with a compound (11) to obtain a compound (16) represented by the following formula (16).

$$CH_3SO_2—OR^{21} \quad (11)$$

$$HO(CH_2)_jQ^F\text{-}[(OCF_2CF_2)_c—(OCF_2CF_2CF_2CF_2)_d]—O\text{-}Q^F(CH_2)_jOR^{21} \quad (16)$$

In the presence of a basic compound (triethylamine, trimethylamine hydrochloride, etc.), a compound (17) represented by the following formula (17) is reacted with mesyl chloride to obtain a compound (18) represented by the following formula (18).

$$(HO)_{m+n}—Y^2 \quad (17)$$

$$(CH_3SO_2—O)_{m+n}—Y^2 \quad (18)$$

The compound (15) and metallic sodium or a basic compound (sodium hydride, potassium tert-butoxide) are reacted and then further reacted with the compound (18) to obtain a compound (19) represented by the following formula (19) and a compound (A61) represented by the following formula (A61).

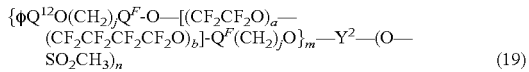
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_m—Y^2—(O—SO_2CH_3)_n \quad (19)$$

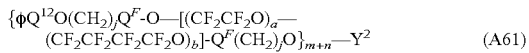
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_{m+n}—Y^2 \quad (A61)$$

The compound (16) and metallic sodium or a basic compound (sodium hydride, potassium tert-butoxide) are reacted and then further reacted with the compound (19) to obtain a compound (A62).

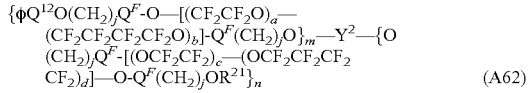
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_m—Y^2—\{O(CH_2)_jQ^F\text{-}[(OCF_2CF_2)_c—(OCF_2CF_2CF_2CF_2)_d]—O\text{-}Q^F(CH_2)_jOR^{21}\}_n \quad (A62)$$

<Method (2-2)>

A production method for a mixture of compounds (A63) represented by the following formula (A63) will be described.

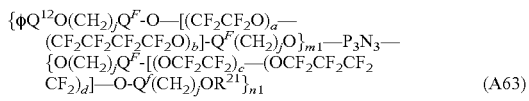
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_{m1}—P_3N_3—\{O(CH_2)_jQ^F\text{-}[(OCF_2CF_2)_c—(OCF_2CF_2CF_2CF_2)_d]—O\text{-}Q^F(CH_2)_jOR^{21}\}_{n1} \quad (A63)$$

Here, $P_3N_3$ is a cyclotriphosphazene structure,
m1 is an integer of from 0 to 6,
n1 is an integer from 0 to 6,
m1+n1=6.
$\{\text{-}Q^F(CH_2)_jO\}_{m1}—P_3N_3—\{O(CH_2)_jQ^F\text{-}\}_{n1}$ corresponds to Y,
$\phi Q^{12}O(CH_2)_jQ^F\text{-}$ is a group (X16),
$\text{-}Q^F(CH_2)_jOR^{21}$ is a group (Z1).

The compound (15) and metallic sodium or a basic compound (sodium hydride, potassium tert-butoxide) are reacted, and then further reacted with a cyclo trimer of phosphonitrile chloride (i.e. hexachlorocyclotriphosphazene) to obtain a mixture of compounds (20) represented by the formula (20).

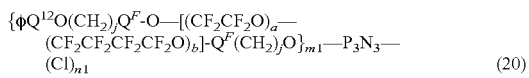
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_{m1}—P_3N_3—(Cl)_{n1} \quad (20)$$

The compound (16) and metallic sodium or a basic compound (sodium hydride, potassium tert-butoxide) are reacted, and then further reacted with the mixture of compounds (20) to obtain a mixture of compounds (A63).

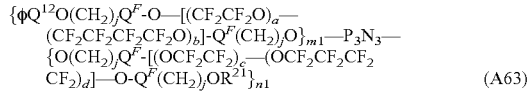
$$\{\phi Q^{12}O(CH_2)_jQ^F\text{-}O—[(CF_2CF_2O)_a—(CF_2CF_2CF_2CF_2O)_b]\text{-}Q^F(CH_2)_jO\}_{m1}—P_3N_3—\{O(CH_2)_jQ^F\text{-}[(OCF_2CF_2)_c—(OCF_2CF_2CF_2CF_2)_d]—O\text{-}Q^F(CH_2)_jOR^{21}\}_{n1} \quad (A63)$$

<Method (3)>

The production method for a compound (13) and a compound (14) will be described with reference to the case of the compound (13). The compound (14) can be produced in the same manner as the compound (13).

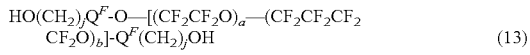
$$HO(CH_2)_jQ^F\text{-}O—[(CF_2CF_2O)_a—(CF_2CF_2CF_2CF_2O)_b]\text{-}Q^F(CH_2)_jOH \quad (13)$$

$$HO(CH_2)_jQ^F\text{-}[(OCF_2CF_2)_c—(OCF_2CF_2CF_2CF_2)_d]—O\text{-}Q^F(CH_2)_jOH \quad (14)$$

<Method (3-1)>

The method (3-1) is a production example for the compound (13) wherein $(CF_2CF_2O)$ units and $(CF_2CF_2CF_2CF_2O)$ units are alternately arranged.

The compound (13) wherein $(CF_2CF_2O)$ units and $(CF_2CF_2CF_2CF_2O)$ units are alternately arranged, can be produced by using a compound (3-1) represented by the following formula (3-1), as the compound (3), when producing the compound (A1) by the method (1-1).

$$HO—CH_2CH_2—OH \quad (3-1)$$

<Method (3-2)>

The method (3-2) is a production example for the compound (13) wherein $(CF_2CF_2O)$ units and $(CF_2CF_2CF_2CF_2O)$ units are randomly arranged.

A compound (21) represented by the following formula (21) is prepared. a1 is an integer of from 1 to 100, and b1 is an integer of from 1 to 100.

$$HO—[(CH_2CH_2O)_{a1}—(CH_2CH_2CH_2CH_2O)_{b1}]—H \quad (21)$$

As commercial products of the compound (21), Polyserine (registered trademark) series (DC-1100, DC-1800E, 60DC-1800, DC-3000E) manufactured by NOF CORPORATION., etc., may be mentioned.

By an esterification reaction of the compound (21) and a compound (5), a compound (22) represented by the following formula (22) is obtained.

$$R^fC(O)F \quad (5)$$

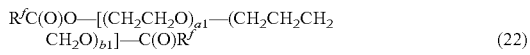
$$R^fC(O)O—[(CH_2CH_2O)_{a1}—(CH_2CH_2CH_2CH_2O)_{b1}]—C(O)R^f \quad (22)$$

A compound (23) represented by the following formula (23) is obtained by substituting hydrogen atoms of the compound (22) by fluorine atoms by using a fluorine gas.

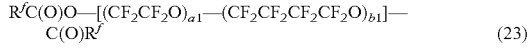
$$R^fC(O)O—[(CF_2CF_2O)_{a1}—(CF_2CF_2CF_2CF_2O)_{b1}]—C(O)R^f \quad (23)$$

The compound (23) is reacted with a compound (8) to obtain a mixture of compounds (24i) to (24iii) represented by the following formulae.

$$R^{11}OH \quad (8)$$

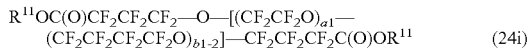
$$R^{11}OC(O)CF_2CF_2CF_2—O—[(CF_2CF_2O)_{a1}—(CF_2CF_2CF_2CF_2O)_{b1\text{-}2}]—CF_2CF_2CF_2C(O)OR^{11} \quad (24i)$$

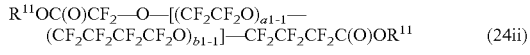
$$R^{11}OC(O)CF_2—O—[(CF_2CF_2O)_{a1\text{-}1}—(CF_2CF_2CF_2CF_2O)_{b1\text{-}1}]—CF_2CF_2CF_2C(O)OR^{11} \quad (24ii)$$

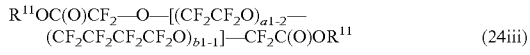
$$R^{11}OC(O)CF_2—O—[(CF_2CF_2O)_{a1\text{-}2}—(CF_2CF_2CF_2CF_2O)_{b1\text{-}1}]—CF_2C(O)OR^{11} \quad (24iii)$$

The mixture of compounds (24i) to (24iii) are reduced with a reducing agent (sodium borohydride, etc.) to obtain a mixture of compounds (13ai) to (13aiii) represented by the following formulae.

$$HOCH_2CF_2CF_2CF_2\text{—}O\text{—}[(CF_2CF_2O)_{a1}\text{—}(CF_2CF_2CF_2CF_2O)_{b1\text{-}2}]\text{—}CF_2CF_2CF_2CH_2OH \quad (13ai)$$

$$HOCH_2CF_2\text{—}O\text{—}[(CF_2CF_2O)_{a1\text{-}1}\text{—}(CF_2CF_2CF_2CF_2O)_{b1\text{-}1}]\text{—}CF_2CF_2CF_2CH_2OH \quad (13aii)$$

$$HOCH_2CF_2\text{—}O\text{—}[(CF_2CF_2O)_{a1\text{-}2}\text{—}(CF_2CF_2CF_2CF_2O)_{b1}]\text{—}CF_2CH_2OH \quad (13aiii)$$

<Method (3-3)>

The method (3-3) is a production example for the compound (13) wherein at least one block composed of a plurality of ($CF_2CF_2O$) units and at least one block composed of a plurality of ($CF_2CF_2CF_2CF_2O$) units are linked.

A compound represented by the following formula (25) and a compound (26) represented by the following formula (26) are prepared. a2 is an integer of from 1 to 51, and b2 is an integer of from 1 to 51.

$$HO\text{—}(CH_2CH_2O)_{a2}\text{—}H \quad (25)$$

$$HO\text{—}(CH_2CH_2CH_2CH_2O)_{b2}\text{—}H \quad (26)$$

As commercial products of the compound (25), polyethylene glycols (PEG# 200T, PEG#200, PEG#300, PEG#400, PEG#600, PEG#1000, PEG#1540, PEG#2000) manufactured by NOF CORPORATION, etc., may be mentioned. As commercial products of the compound (26), Uniol (registered trademark) series (PB-500, PB-700, PB-1000, PB-2000, PB-4800) manufactured by NOF CORPORATION., etc., may be mentioned.

In the presence of a basic compound (triethylamine, trimethylamine hydrochloride, etc.), the compound (25) or the compound (26) is reacted with mesyl chloride to obtain a compound (27) represented by the following formula (27) or a compound (28) represented by the following formula (28).

$$CH_3SO_2\text{—}O\text{—}(CH_2CH_2O)_{a2}\text{—}SO_2CH_3 \quad (27)$$

$$CH_3SO_2\text{—}O\text{—}(CH_2CH_2CH_2CH_2O)_{b2}\text{—}SO_2CH_3 \quad (28)$$

The compound (26) and metallic sodium or a basic compound (sodium hydride, potassium tert-butoxide) are reacted, and then further reacted with the compound (27) to obtain a compound (29i) represented by the following formula (29i). Or the compound (25) and metallic sodium or a basic compound (sodium hydride, potassium tert-butoxide) are reacted, and then further reacted with the compound (28) to obtain a compound (29ii) represented by the following formula (29ii).

$$HO\text{—}(CH_2CH_2O)_{a2}\text{—}(CH_2CH_2CH_2CH_2O)_{b2}\text{—}(CH_2CH_2O)_{a2}\text{—}H \quad (29i)$$

$$HO\text{—}(CH_2CH_2CH_2CH_2O)_{b2}\text{—}(CH_2CH_2O)_{a2}\text{—}(CH_2CH_2CH_2CH_2O)_{b2}\text{—}H \quad (29ii)$$

By an esterification reaction of the compound (29i) or the compound (29ii) with a compound (5), a compound (30i) represented by the following formula (30i) or a compound (30ii) represented by the following formula (30ii) is obtained.

$$R^fC(O)F \quad (5)$$

$$R^fC(O)O\text{—}(CH_2CH_2O)_{a2}\text{—}(CH_2CH_2CH_2CH_2O)_{b2}\text{—}(CH_2CH_2O)_{a2}\text{—}C(O)R^f \quad (30i)$$

$$R^fC(O)O\text{—}(CH_2CH_2CH_2CH_2O)_{b2}\text{—}(CH_2CH_2O)_{a2}\text{—}(CH_2CH_2CH_2CH_2O)_{b2}\text{—}C(O)R^f \quad (30ii)$$

A compound (31 i) represented by the following formula (31 i) or a compound (31 ii) represented by the following formula (31 ii) is obtained by substituting hydrogen atoms of the compound (30i) or the compound (30ii) by fluorine atoms by using a fluorine gas.

$$R^fC(O)O\text{—}(CF_2CF_2O)_{a2}\text{—}(CF_2CF_2CF_2CF_2O)_{b2}\text{—}(CF_2CF_2O)_{a2}\text{—}C(O)R^f \quad (31i)$$

$$R^fC(O)O\text{—}(CF_2CF_2CF_2CF_2O)_{b2}\text{—}(CF_2CF_2O)_{a2}\text{—}(CF_2CF_2CF_2CF_2O)_{b2}\text{—}C(O)R^f \quad (31ii)$$

The compound (31i) or the compound (31ii) is reacted with a compound (8) to obtain a compound (32i) represented by the following formula (32i) or a compound (32ii) represented by the following formula (32ii).

$$R^{11}OH \quad (8)$$

$$R^{11}OC(O)CF_2O\text{—}(CF_2CF_2O)_{a2\text{-}1}\text{—}(CF_2CF_2CF_2CF_2O)_{b2}\text{—}(CF_2CF_2O)_{a2\text{-}1}\text{—}CF_2C(O)OR^{11} \quad (32i)$$

$$R^{11}OC(O)CF_2CF_2CF_2O\text{—}(CF_2CF_2CF_2CF_2O)_{b2\text{-}1}\text{—}(CF_2CF_2O)_{a2}\text{—}(CF_2CF_2CF_2CF_2O)_{b2\text{-}1}\text{—}CF_2CF_2CF_2C(O)OR^{11} \quad (32ii)$$

The compound (32i) or the compound (32ii) is reduced by a reducing agent (sodium borohydride, etc.) to obtain a compound (13bi) represented by the following formula (13bi) or a compound (13bii) represented by the following formula (13bii).

$$HOCH_2CF_2\text{—}O\text{—}(CF_2CF_2O)_{a2\text{-}1}\text{—}(CF_2CF_2CF_2CF_2O)_{b2}\text{—}(CF_2CF_2O)_{a2\text{-}1}\text{—}CF_2CH_2OH \quad (13bi)$$

$$HOCH_2CF_2CF_2CF_2\text{—}O\text{—}(CF_2CF_2CF_2CF_2O)_{b2\text{-}1}\text{—}(CF_2CF_2O)_{a2}\text{—}(CF_2CF_2CF_2CF_2O)_{b2\text{-}1}\text{—}CF_2CF_2CF_2CH_2OH \quad (13bii)$$

(Advantageous Effects)

In the fluorinated polyether compound (A) as described above, its polyether chain is composed of ($CF_2CF_2O$) units and ($CF_2CF_2CF_2CF_2O$) units, and thus is excellent in flexibility as compared with a polyether chain composed solely of ($CF_2CF_2O$) units. Therefore, the fluorinated polyether compound (A) having a polyether chain composed of ($CF_2CF_2O$) units and ($CF_2CF_2CF_2CF_2O$) units is excellent in lubricity.

Further, the fluorinated polyether compound (A) having no —$OCF_2O$— structure is excellent in chemical stability, as compared with a fluorinated polyether compound having a —$OCF_2O$— structure. Further, as compared with the fluorinated polyether compound having a —$OCF_2O$— structure, the linearity is high, and it will not be in a random coil state, whereby it is possible to cope with thinning of the coating film.

Further, when X in the formula (A) is a $HOCH_2CH(OH)CH_2OCH_2CF_2CF_2CF_2$— group or a $HOCH_2CH(OH)CH_2OCH_2CF_2$— group, it will be excellent in adhesion to the substrate.

[Fluorinated Polyether Compound (B)]

A second embodiment of the fluorinated polyether compound of the present invention is a fluorinated polyether compound (B) represented by the following formula (B) (hereinafter referred to also as the compound (B)).

$$X\text{—}O\text{—}[(CF_2CF_2O)_g\text{—}(CF_2CF_2CF_2CF_2O)_h]\text{—}W \quad (B)$$

(Group X)

X is a group having a hydroxy group, a carboxy group, an ester group or an aryl group.

Examples and preferred embodiments of X are the same as X in the fluorinated polyether compound (A) and therefore, their details will be omitted.

Hereinafter, also with respect to the same reference numerals as in the fluorinated polyether compound (A), details will be omitted.

(Group W)

W is a group having a hydroxy group, a carboxy group, an ester group, an aryl group, or a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms.

W may, for example, be a group (W1) represented by the following formula (W1) or a group (W2) represented by the following formula (W2). $R^2$ is a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms.

$$-Q^1-(X^1)_i \quad (W1)$$

$$-R^2 \quad (W2)$$

Group (W1) may, for example, be a group (W11) represented by the following formula (W11), a group (W12) represented by the following formula (W12), a group (W13) represented by the following formula (W13), a group (W14) represented by the following formula (W14), a group (W15) represented by the following formula (W15), or a group (W16) represented by the following formula (W16).

$$-Q^F(CH_2)_j-OH \quad (W11)$$

$$-Q^F(CH_2)_jOQ^{11}-(OH)_i \quad (W12)$$

$$-Q^F-C(O)OH \quad (W13)$$

$$-Q^F(CH_2)_j-OC(O)R^{11} \quad (W14)$$

$$-Q^F-C(O)OR^{11} \quad (W15)$$

$$-Q^F(CH_2)_j-OQ^{12}-\phi \quad (W16)$$

Group (W2) may, for example, be a group (W21) represented by the following formula (W21).

$$-Q^F(CH_2)_jOR^{21} \quad (W21)$$

W is preferably group (W12) wherein i is 2, from the viewpoint of excellent adhesion to the carbon protective film, particularly preferably the following groups, since the compound will be easy to produce and will be excellent in stability.

—$CF_2CF_2CF_2CH_2OCH_2CH(OH)CH_2OH$

—$CF_2CH_2OCH_2CH(OH)CH_2OH$ (Polyether Chain)

A polyether chain in the compound (B) is composed of $(CF_2CF_2O)$ units and $(CF_2CF_2CF_2CF_2O)$ units. A polyether chain composed solely of $(CF_2CF_2O)$ units is insufficient in flexibility, therefore a fluorinate polyether compound having such a chain is insufficient in lubricity. By introducing $(CF_2CF_2CF_2CF_2O)$ units in such a chain, the polyether chain will be relatively flexible, and a fluorinated polyether compound having such a chain will be excellent in lubricity.

The polyether chain preferably has a structure in which $(OCF_2CF_2)$ units and $(OCF_2CF_2CF_2)$ units are alternately arranged, whereby the flexibility of the polyether chain will be sufficient, and uniformity of the flexibility in the chain will be excellent.

$$<[(CF_2CF_2O)_g-(CF_2CF_2CF_2CF_2O)_h]>$$

g is an integer from 1 to 200, preferably from 1 to 100, particularly preferably from 1 to 40, whereby the compound (B) will be excellent in solubility in a solvent, viscosity and lubricity.

h is an integer of from 1 to 200, preferably from 1 to 100, particularly preferably from 1 to 40, whereby the compound (B) will be excellent in solubility in a solvent, viscosity and lubricity.

h/(g+h) is preferably from 0.2 to 0.8, more preferably from 0.3 to 0.7, particularly preferably from 0.4 to 0.6, whereby the flexibility of the polyether chain will be sufficient, and the compound (B) will be excellent in lubricity.

In $[(CF_2CF_2O)_g-(CF_2CF_2CF_2CF_2O)_h]$, the linking order of g number of $(CF_2CF_2O)$ units and h number of $(CF_2CF_2CF_2CF_2O)$ units is not limited. That is, $(CF_2CF_2O)$ units and $(CF_2CF_2CF_2CF_2O)$ units may be randomly located, $(CF_2CF_2O)$ units and $(CF_2CF_2CF_2CF_2O)$ units may be alternately arranged, or at least one block composed of a plurality of $(CF_2CF_2O)$ units and at least one block composed of a plurality of $(CF_2CF_2CF_2CF_2O)$ units may be linked. As flexibility of the polyether chain will be sufficient, and uniformity of the flexibility in the chain will be excellent, $[(CF_2CF_2O)_g-(CF_2CF_2CF_2CF_2O)_h]$ preferably has a structure wherein $(CF_2CF_2O)$ units and $(CF_2CF_2CF_2CF_2O)$ units are alternately arranged, and more preferably has at least 50%, further preferably at least 80%, particularly preferably at least 90% of such an alternately arranged structure in the polyether chain.

(—$OCF_2O$— structure)

The compound (B) preferably has no —$OCF_2O$— structure for the same reason as the fluorinated polyether compound (A).

(Number Average Molecular Weight)

The number average molecular weight of the compound (B) is preferably from 500 to 50,000, more preferably from 500 to 10,000, particularly preferably from 1,000 to 5,000, for the same reason as the fluorinated polyether compounds (A).

(Production Method for Fluorinated Polyether Compound (B))

The fluorinated polyether compound (B) may be produced in the same manner as the fluorinated polyether compound (A). Further, it may also be obtained as an intermediate obtainable in the production process for the fluorinated polyether compound (A).

For example, a compound (B1) represented by the following formula (B1) is obtainable by the above-described method (3-1). $(CF_2CF_2O)$ units and $(CF_2CF_2CF_2CF_2O)$ units are alternately arranged except for some.

$$HO(CH_2)_jQ^F-O-[(CF_2CF_2O)_g-(CF_2CF_2CF_2CF_2O)_h]-Q^F(CH_2)_jOH \quad (B1)$$

Further, a compound (B2) represented by the following formula (B2) is obtainable from the compound (B1) by the last step of the above-described method (1-1).

$$HOCH_2CH(OH)CH_2O(CH_2)_jQ^F-O-[(CF_2CF_2O)_g-(CF_2CF_2CF_2CF_2O)_h]-Q^F(CH_2)_jOCH_2CH(OH)CH_2OH \quad (B2)$$

The compounds (24i) to (24iii) and the compound (13ai) to (13aiii) obtained by the above-described method (3-2), also correspond to the fluorinated polyether compound (B).

The compound (32i), the compound (32ii), the compound (13bi) and the compound (13bii) obtained by the above-described method (3-3), also correspond to the fluorinated polyether compound (B).

The compound (15) and the compound (16) obtained by the above-described method (2-1) also correspond to the fluorinated polyether compound (B).

Further, the production method for the fluorinated polyether compound (B) is not limited thereto.

(Advantageous Effects)

In the above-described fluorinated polyether compound (B), a polyether chain is composed of $(CF_2CF_2O)$ units and $(CF_2CF_2CF_2CF_2O)$ units, and thus is excellent in flexibility as compared with a polyether chain composed solely of $(CF_2CF_2O)$ units. Therefore, a fluorinated polyether compound (B) having a polyether chain composed of $(CF_2CF_2O)$ units and $(CF_2CF_2CF_2CF_2O)$ units, is excellent in lubricity.

Further, the fluorinated polyether compound (B) has no —$OCF_2O$— structure, whereby it is excellent in chemical stability as compared with a fluorinated polyether compound having a —$OCF_2O$— structure. Further, as compared with the fluorinated polyether compound having a —$OCF_2O$— structure, the linearity is high, and it will not be in a random coil state, whereby it is possible to cope with thinning of the coating film.

Further, when X in the formula (B) is a $HOCH_2CH(OH)CH_2OCH_2CF_2CF_2CF_2$— group or a $HOCH_2CH(OH)CH_2OCH_2CF_2$— group, the adhesion to the substrate will be excellent.

[Applications of Fluorinated Polyether Compound]

The fluorinated polyether compound of the present invention is useful as a surface modifier or a surfactant. As the surface modifier, a lubricant, etc. may be mentioned.

As other applications of the fluorinated polyether compound of the present invention, a wire coating material, an ink repellent (e.g. for coating, for printing equipment such as an ink jet, etc.), an adhesive for a semiconductor device (e.g. adhesive for LOC (lead-on-chip) tape), a semiconductor protective coating (e.g. a moisture-proof coating agent, a solder creeping up inhibitor), an additive to a thin film (e.g. a pellicle film, etc.) used in the optical field, a lubricant for the antireflection film for displays, an antireflection film for resist, etc. may be mentioned.

The fluorinated polyether compound of the invention is preferably used in an application for forming a film (surface layer) containing the fluorinated polyether compound of the present invention on a substrate.

The surface layer maintains high lubricity, since it contains the fluorinated polyether compound of the present invention having a hydroxy group, a carboxy group, an ester group or an aryl group at its molecular terminals. Therefore, by providing such a surface layer on a substrate, it is possible to impart a function such as lubricity. Further, the surface layer has high adhesion to the substrate and is excellent in durability. Further, the surface layer is transparent, has a low refractive index and is excellent in heat resistance or chemical resistance.

The shape and material of the substrate are not particularly limited and may suitably be selected for use to meet the particular application of the substrate having such a surface layer. As applications of the substrate having such a surface layer, a magnetic disk, an optical fiber, a mirror, a solar cell, an optical disk, a touch panel, a photosensitive and fixing drum, a film capacitor, various films such as antireflection films for glass windows, etc. may be mentioned.

The thickness of the surface layer is appropriately set depending on the particular application.

The thickness of the surface layer may be calculated, for example, from the oscillation period of an interference pattern by obtaining the interference pattern of reflected X-ray by an X-ray reflectance method using an X-ray diffractometer for thin film analysis (manufactured by RIGAKU Co., ATX-G).

A liquid medium may be added to the fluorinated polyether compound of the present invention to obtain a liquid composition. In particular, in a case where the fluorinated polyether compound of the present invention is to be used in an application to form a surface layer on a substrate as a surface modifier, it is preferred to use it in the form of a liquid composition by adding a liquid medium to the fluorinated polyether compound of the present invention.

[Lubricant]

The lubricant of the present invention contains the fluorinated polyether compound of the present invention. The lubricant of the present invention may contain one type of the fluorinated polyether compound (A) alone, or may contain two or more types of the fluorinated polyether compound (A) different in at least one of X, Y, Z, m, n and a to d in the formula (A), in combination. Further, it may contain one type of the fluorinated polyether compound (B) alone, or may contain two or more types of the fluorinated polyether compound (B) different in at least one of X, W, g and h in the formula (B), in combination. Also, it may contain the fluorinated polyether compound (A) and the fluorinated polyether compound (B).

The lubricant of the present invention may consist solely of the fluorinated polyether compound of the present invention, or may further contain other components.

The content of the fluorinated polyether compound of the present invention in the lubricant of the present invention, is preferably from 90 to 100 mass %, particularly preferably 100 mass %, based on the total mass of the lubricant. That is, the lubricant of the present invention is particularly preferably composed solely of the fluorinated polyether compound of the present invention.

As other components, optional compounds which are usable as lubricants and which do not correspond to the fluorinated polyether compound of the present invention, may be used. For example, a fluorinated polyether compound other than the fluorinated polyether compound of the present invention, or a coupling agent of e.g., silane type, epoxy type, titanium type or aluminum type, may be mentioned. When the fluorinated polyether compound of the present invention is used as a lubricant, it is possible to improve the adhesion between the substrate and the fluorinated polyether compound of the present invention by using such a coupling agent.

The application of the lubricant is preferably for a magnetic disk, particularly an application to impart lubricity by applying it on a diamond-like carbon protective film (DLC film) of a magnetic disk.

The magnetic disk may, for example, be one having, on a NiP-plated substrate (aluminum, glass, etc.), a primer layer, a magnetic recording layer and a diamond-like carbon protective film (DLC film) in this sequence. The thickness of the DLC film is preferably at most 5 nm. The average surface roughness of the DLC film (Ra) is preferably at most 2 nm.

In the case of a surface layer formed by applying the lubricant to a DLC film of the magnetic disk, the thickness thereof is preferably from 0.1 to 2 nm, particularly preferably from 0.5 to 1 nm. When the thickness of the surface layer is at least the above lower limit, the lubricating effect, etc. by the surface layer can be obtained sufficiently. When the thickness of the surface layer is at most the above upper limit, it can contribute to a higher recording density of the magnetic disk. The fluorinated polyether compound of the present invention is able to form a surface layer that exhibits sufficient lubricity even when made thin. Therefore, the thinner the thickness of the surface layer, the higher the usefulness of the present invention.

[Liquid Composition]

The liquid composition of the present invention comprises the fluorinated polyether compound of the present invention and a liquid medium.

The liquid composition of the invention may be a solution, a suspension or an emulsion, and is preferably a solution.

The concentration of the fluorinated polyether compound of the present invention in the liquid composition can be adjusted appropriately depending upon the particular application, and is preferably from 0.005 to 50 mass %, more preferably from 0.005 to 5 mass %, particularly preferably from 0.01 to 1 mass %, based on the total mass of the liquid composition. When the concentration of the fluorinated polyether compound of the present invention is within the above range, a uniform surface layer can be formed.

The liquid medium may be any one so long as it is capable of dissolving or dispersing the fluorinated polyether compound of the present invention, and an organic solvent is preferred. The organic solvent may be a fluorinated organic solvent or a non-fluorinated organic solvent, or it may contain both of such solvents.

The fluorinated organic solvent may, for example, be a fluoroalkane, a fluoro-aromatic compound, a fluoroalkyl ether, a fluoroalkyl amine, a fluoro-alcohol, etc.

The fluoroalkane is preferably a $C_{4-8}$ compound. As commercial products, for example, $C_6F_{13}H$ (manufactured by Asahi Glass Co., Ltd., AC-2000), $C_6F_{13}C_2H_5$ (manufactured by Asahi Glass Co., Ltd., AC-6000), $C_2F_5CHFCHFCF_3$ (manufactured by DuPont, Vertrel (registered trademark) XF), etc. may be mentioned.

The fluoro-aromatic compound may, for example, be hexafluorobenzene, trifluoromethyl benzene, perfluorotoluene, bis(trifluoromethyl)benzene, etc.

The fluoroalkyl ether compound is preferably a $C_{4-12}$ compound. The fluoroalkyl ether is preferably a hydrofluoroalkyl ether. As commercial products, for example, $CF_3CH_2OCF_2CF_2H$ (manufactured by Asahi Glass Company, AE-3000), $C_4F_9OCH_3$ (manufactured by 3M Co., Novec (registered trademark)-7100), $C_4F_9OC_2H_5$ (manufactured by 3M Co., Novec (registered trademark)-7200), $C_6F_{13}OCH_3$ (manufactured by 3M Co., Novec (registered trademark)-7300), etc. may be mentioned.

The fluoroalkyl amine is preferably a perfluoroalkyl amine, and, for example, perfluorotripropylamine, perfluorotributylamine, etc. may be mentioned.

The fluoro-alcohol may, for example, be 2,2,3,3-tetrafluoropropanol, 2,2,2-trifluoroethanol, hexafluoroisopropanol, etc.

As the fluorinated organic solvent, from the viewpoint of solubility of the fluorinated polyether compound, a fluoroalkane, a fluoro-aromatic compound or a fluoroalkyl ether is preferred. Among them, from the viewpoint of lower ozone depletion, a hydrofluoroalkyl ether is particularly preferred.

The non-fluorinated organic solvent is preferably a compound composed solely of hydrogen atoms and carbon atoms, or a compound composed solely of hydrogen atoms, carbon atoms and oxygen atoms, and for example, a hydrocarbon-type solvent, an alcohol-type organic solvent, a ketone-type organic solvent, an ether-type organic solvent or an ester-type organic solvent, may be mentioned.

The hydrocarbon-type organic solvent is preferably hexane, heptane, cyclohexane, etc.

The alcohol-type organic solvent is preferably methanol, ethanol, propanol, isopropanol, etc.

The ketone-type organic solvent is preferably acetone, methyl ethyl ketone, methyl isobutyl ketone, etc.

The ether-type organic solvent is preferably diethyl ether, tetrahydrofuran, ethylene glycol dimethyl ether, etc.

The ester-type organic solvent is preferably ethyl acetate, butyl acetate, etc.

As the non-fluorinated organic solvent, from the viewpoint of solubility of the fluorinated polyether compound, a ketone-type organic solvent is particularly preferred.

The liquid medium is preferably at least one organic solvent selected from the group consisting of a fluoroalkane, a fluoro-aromatic compound, a fluoroalkyl ether, a compound composed solely of hydrogen atoms and carbon atoms, and a compound composed solely of hydrogen atoms, carbon atoms and oxygen atoms. Particularly, a fluorinated organic solvent selected from a fluoroalkane, a fluoro-aromatic compound and a fluoroalkyl ether is preferred.

As the liquid medium, it is preferred to contain at least one organic solvent selected from the group consisting of, as fluorinated organic solvents, a fluoroalkane, a fluoro-aromatic compound and a fluoroalkyl ether, and, as a non-fluorinated organic solvent, a compound composed solely of hydrogen atoms, carbon atoms and oxygen atoms, in an amount of at least 90 mass % in total of the entire liquid medium, with a view to increasing the solubility of the fluorinated polyether compound.

The liquid composition may further contain, if necessary, other components other than the fluorinated polyether compound of the present invention and the liquid medium, within a range not impair the effects of the present invention.

As such other components, a radical scavenger (e.g. manufactured by Dow Chemicals Co., X-1p), etc. may be mentioned.

The liquid composition should better not contain metal ions, anions, moisture, low molecular polar compounds, etc., since otherwise, the desired performance may not be attained.

Metal ions (Na, K, Ca, Al, etc.) are likely to be bonded with anions to form a Lewis acid catalyst, which may promote a decomposition reaction of the fluorinated polyether compound. Anions (F, Cl, $NO_2$, $NO_3$, $PO_4$, $SO_4$, $C_2O_4$, etc.) and moisture, may corrode the surface of the substrate. Therefore, the water content in the liquid composition is preferably at most 2,000 ppm.

Low molecular polar compounds (alcohols; plasticizers eluted from the resin, etc.) may reduce the adhesion between the substrate and the surface layer.

[Method of Using Fluorinated Polyether Compound]

As a method of using the fluorinated polyether compound or the liquid composition, a known method may be applied depending on the particular purpose.

For example, in the case of using the fluorinated polyether compound of the present invention as a lubricant, it is preferred that the fluorinated polyether compound of the present invention is applied onto a substrate, or the liquid composition containing the fluorinated polyether compound of the invention is applied onto a substrate and dried (i.e. the liquid medium is removed from the liquid composition) to form a film (surface layer) containing the fluorinated polyether compound of the present invention, thereby to let the desired function be exhibited.

The substrate to be coated with the fluorinated polyether compound of the present invention or the liquid composition containing it, is not particularly limited, and, for example, the same one as mentioned above as the substrate on which the surface layer is formed, may be mentioned. As the substrate, a magnetic disk is preferred from the viewpoint of usefulness of the present invention.

The method for applying the fluorinated polyether compound or the liquid composition containing it, may, for example, be a roll coating method, a casting method, a dip coating method, a spin coating method, a water casting method, a die coating method, a Langmuir-Blodgett method, a vacuum deposition method, etc., and a spin coating method, a dip coating method, or a vacuum deposition method is preferred.

When the liquid composition is applied, the drying method may, for example, be natural drying, vacuum drying, centrifugal drying, heat drying, etc.

After forming the surface layer containing the fluorinated polyether compound of the present invention on a substrate, adhesion treatment may be carried out in order to firmly adhere the fluorinated polyether compound of the present invention on the substrate (for example, on the carbon protective film of the magnetic disk).

As such adhesion treatment, heat treatment, infrared irradiation treatment, ultraviolet irradiation treatment, plasma treatment, etc. may be mentioned, and heat treatment or ultraviolet irradiation treatment is preferred, and heat treatment is particularly preferred. Drying treatment may also serve as adhesion treatment.

Further, the substrate after adhesion treatment may be washed with a fluorinated organic solvent for the purpose of removal of deposits or removal of an excess fluorinated polyether compound.

[Article]

The article of the present invention is one having a film containing the fluorinated polyether compound of the present invention, on a substrate.

The substrate on which the liquid composition of the present invention is to be applied, is not particularly limited, and it may, for example, be the same one as mentioned above, as the substrate on which the surface layer is to be provided. As the substrate, a magnetic disk is preferred from the viewpoint of usefulness of the present invention.

As a method for providing such a film on a substrate, a known method as a method of forming a film made of a fluorinated polyether compound, may be utilized. For example, such a film may be formed by the above-described method of forming the surface layer by applying the liquid composition of the present invention onto a substrate.

EXAMPLES

Now, the present invention will be described in detail with reference to Examples. However, it should be understood that the present invention is by no means limited by these Examples.

Ex. 1, 2, 5 to 8 are Examples of the present invention, and Ex. 3 and 4 are Comparative Examples.

The evaluation methods in each Ex. are shown below.

[Evaluation Methods]

(GPC Analysis)

The number average molecular weight (Mn) and the molecular weight distribution (Mw/Mn) were measured by gel permeation chromatography (hereinafter referred to also as GPC). Here, Mw indicates the mass average molecular weight.

Measurements by GPC were conducted in accordance with the method disclosed in JP-A-2001-208736, under the following conditions.

Mobile phase: a mixed solvent of R-225 (manufactured by Asahi Glass Co., Ltd., ASAHIKLIN AK-225SEC Grade 1) and hexafluoroisopropyl alcohol (R-225: hexafluoroisopropyl alcohol=99:1 (volume ratio)).

Analytical column: Two PLgel MIXED-E columns (manufactured by Polymer Laboratories) are linked in series.

Standard samples for molecular weight measurement: four types of perfluoropolyether with Mw/Mn being less than 1.1 and Mn being from 2,000 to 10,000, and one type of perfluoropolyether with Mw/Mn being at least 1.1 and Mn being 1,300.

Mobile phase flow rate: 1.0 mL/min.

Column temperature: 37° C.

Detector: evaporative light scattering detector.

(Dynamic Friction Coefficient Measurement)

The dynamic friction coefficient of the outermost surface of an article having a surface layer provided on a substrate (the location provided with the surface layer on the surface of the article) was measured by using a friction measuring instrument (manufactured by Heidon Co., Tribogear). Using a SUS ball of φ10 mm as a contactor, the measurement was made under a load of 100 g with a moving distance of 20 mm at a moving speed of 1 mm/sec. It was evaluated by the following standards.

○ (Good): the dynamic friction coefficient is 1.7 or less.

x (Bad): the dynamic friction coefficient exceeds 1.7.

(Measurement of F/Si)

Coverage of the surface layer provided on a substrate (silicon wafer), was evaluated by the following standards from F/Si measured under the following measuring conditions by X-ray photoelectron spectroscopy (XPS: X-ray Photoelectron Spectroscopy).

○ (Good): F/Si is from 0.8 to 1.0.

x (Bad): F/Si is less than 0.8, or exceeds 1.0.

XPS is a method wherein characteristic X-rays of Al, Mg, etc. are permitted to enter into a sample, and the kinetic energy and the intensity of photoelectrons emitted by the photoelectric effects, are measured, to know the types and amounts of atoms, the chemical bonding states, etc., present on the solid surface.

The kinetic energy Ek of photoelectrons emitted from the sample is a value (Ek=hv−Eb−W) obtained by subtracting the binding energy Eb and the work function W from the incident X-ray energy hv (h: Planck's constant, v: vibration frequency). The binding energy Eb is a value that depends on the type of atoms whereby photoelectrons have been captured in the sample, the electron orbits, and the chemical bonding states. The incident X-ray energy hv and the work function W are known. Therefore, by measuring the kinetic energy Ek, it is possible to obtain the binding energy Eb, and it is possible to know the types of atoms, the electron orbits and the chemical bonding states in the sample.

Incident X-rays are permitted to penetrate to a depth of about several μm of the sample. However, electrons emitted from atoms at a deep location tend to lose their energy by e.g. inelastic scattering with electrons that are bound to other atoms in the sample and will not be emitted from the sample. Therefore, the electrons emitted from the very outermost surface in a depth at a level of several nm as determined by the inelastic mean free path (the distance where the electrons can advance without causing inelastic scattering), are observed as photoelectrons. Thus, XPS is a method of measuring the types and amounts of atoms and the chemical bonding states present on the outermost surface of the sample, with high sensitivity, and it is possible to detect a very thin film which is coated on a substrate with high sensitivity, and thus is an effective method to evaluate the coverage of such a thin film.

When the XPS measurement of the outermost surface of an article (an article using a silicon wafer as a substrate and having a surface layer formed by a lubricant containing a fluorinated polyether compound on the substrate) obtained in each Ex. given hereinafter, is conducted, at a portion covered with the surface layer on the substrate, the intensity of photoelectrons emitted from the 1s orbital of fluorine atoms in the surface layer (hereinafter referred to as the F1s peak intensity) is strongly detected, and the intensity of photoelectrons emitted from the Si2p orbital of silicon atoms in the substrate (hereinafter referred to as the Si2p peak intensity) is weakly detected or is not detected. In contrast, at a portion not covered by the surface layer on the substrate, photoelectrons emitted from fluorine atoms are not detected, and the intensity of photoelectrons emitted from the Si2p orbital of silicon atoms is strongly detected. Therefore, the ratio of the F atom concentration and the Si atom concentration calculated from the F1s peak intensity and the Si2p peak intensity obtained by the XPS measurement, is considered to have a positive correlation with the coverage of the surface layer provided on the substrate.

As the XPS device, PHI Quantera SXM manufactured by ULVAC-PHI, Inc., was used. Using $AlK_\alpha$ rays (1486.6 eV) focused in a diameter of about 50 μm as an X-ray source, the measurement was conducted at an irradiated X-ray intensity of 12.4 W, with a pass energy of the detector being 224 eV, at a photoelectron-taking out angle of 45°. The irradiated X-rays were measured as fixed without scanning; measurement of the outer most surface of the sample was carried out, and no etching of the sample was carried out. Further, for charge correction due to the photoelectron-emission from the sample, an electron beam and $Ar^+$ neutralizing gun attached to the device were used. In the calculation of the F1s peak intensity, within a range of a binding energy of from 682 to 691 eV, and in the calculation of the Si2p peak intensity, within a range of a binding energy of from 96 to 107 eV, the integrated intensities of the peaks obtained by removing background were used. Further, the F atom concentration and the Si atom concentration were calculated by using the relative sensitivity coefficients of the respective elements specific to the device.

Ex. 1

Ex. 1-1

Into a 300 mL three-necked round-bottomed flask, 14.1 g of sodium borohydride powder was put, and 350 g of AK-225 (manufactured by Asahi Glass Co., Ltd.) was added. While cooling in an ice bath and stirring under a nitrogen atmosphere, a solution prepared by mixing 100 g of the compound (1), 15.8 g of methanol and 22 g of AK-225, was slowly dropwise added from a dropping funnel, so that the inner temperature would not exceed 10° C. After dropwise addition of the entire amount, a solution prepared by mixing 10 g of methanol and 10 g of AK-225 was further dropwise added. Then, the ice bath was removed, and stirring was continued while slowly warming to room temperature. After stirring for 12 hours at room temperature, the mixture was cooled again in an ice bath, and an aqueous hydrochloric acid solution was dropwise added until the liquid became acidic. After completion of the reaction, the reaction solution was washed once with water and once with a saturated sodium chloride aqueous solution, whereupon the organic phase was recovered. The recovered organic phase was dried over magnesium sulfate, then the solid was filtered by a filter, and the filtrate was concentrated by an evaporator. The recovered concentrate was distilled under reduced pressure to obtain 80.6 g (yield: 88%) of a compound (2).

$$CF_2=CFOCF_2CF_2CF_2C(O)OCH_3 \quad (1)$$

$$CF_2=CFOCF_2CF_2CF_2CH_2OH \quad (2)$$

NMR Spectrum of Compound (2):
$^1$H-NMR (300.4 MHz, solvent: deuterated chloroform, standard: tetramethyl silane (hereinafter referred to as TMS)) δ (ppm): 2.2 (1H), 4.1 (2H).
$^{19}$F-NMR (282.7 MHz, solvent: deuterated chloroform, standard: $CFCl_3$) δ (ppm): −85.6 (2F), −114.0 (1F), −122.2 (1F), −123.3 (2F), −127.4 (2F), −135.2 (1F).

Ex. 1-2

Into a 500 mL eggplant flask connected to a reflux condenser, 100 g of the compound (2), 11.0 g of the compound (3-1) and 25.2 g of potassium carbonate powder were added. Under a nitrogen atmosphere, after stirring for 1 hour at 75° C., the temperature was raised to 120° C., and while controlling the internal temperature to be at most 130° C., 200 g of the compound (2) was dropwise added. After the dropwise addition of the entire amount, stirring was further continued for 1 hour at 120° C. It was confirmed by NMR that a vinyl ether group in the compound (2) had completely disappeared. By adding a hydrochloric acid aqueous solution, excess potassium carbonate was treated, and water and AK-225 were added to carry out liquid separation treatment. After washing three times with water, the organic phase was recovered and concentrated by an evaporator to obtain 310 g of a compound (4-1) represented by the following formula (4-1). Again, it was diluted with 110 g of AK-225, and developed and fractionated by silica gel column chromatography (developing solvent: AK-225, ethyl acetate) for removal of impurities and purification of the molecular weight to obtain 150 g of the compound (4-1).

$$HO-CH_2CH_2-OH \quad (3-1)$$

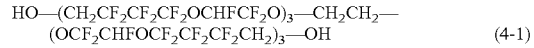

$$HO-(CH_2CF_2CF_2CF_2OCHFCF_2O)_3-CH_2CH_2-(OCF_2CHFOCF_2CF_2CF_2CH_2)_3-OH \quad (4-1)$$

NMR Spectrum of Compound (4-1):
$^1$H-NMR (300.4 MHz, solvent: deuterated acetone, standard: TMS) δ (ppm): 3.4 to 4.0 (8H), 4.3 (8H), 5.8 to 7.0 (6H).
$^{19}$F-NMR (282.7 MHz, solvent: deuterated acetone, standard: $CFCl_3$) δ (ppm): −84.3 to −85.1 (12F), −89.4 to −90.5 (12F), −120.2 (8F), −122.0 (4F), −126.6 (8F), −127.0 (4F), −145.1 (6F).

Ex. 1-3

Into a 300 mL eggplant flask connected to a reflux condenser, 100 g of the compound (4-1) and 9.0 g of sodium fluoride powder were put, and 40 g of a compound (5-1) represented by the following formula (5-1) was added. Under a nitrogen atmosphere, after stirring at 50° C. for 13 hours, stirring was continued for 3 hours at 70° C. After removing the sodium fluoride powder by a press filter, excess compound (5-1) and AK-225 were removed under reduced pressure, to obtain 130 g (yield: 97%) of a compound (6-1) represented by the following formula (6-1).

$$CF_3CF_2CF_2OCF(CF_3)C(O)F \qquad (5\text{-}1)$$

$$\begin{aligned}&CF_3CF_2CF_2OCF(CF_3)C(O)O-\\&\quad(CH_2CF_2CF_2CF_2OCHFCF_2O)_3-CH_2CH_2-\\&\quad(OCF_2CHFOCF_2CF_2CH_2)_3-OC(O)CF\\&\quad(CF_3)OCF_2CF_2CF_3\end{aligned} \qquad (6\text{-}1)$$

NMR Spectrum of Compound (6-1):
$^1$H-NMR (300.4 MHz, solvent: deuterated chloroform, standard: TMS) δ (ppm): 3.4 to 4.0 (8H), 4.3 (4H), 4.9 (4H), 5.8 to 7.0 (6H).
$^{19}$F-NMR (282.7 MHz, solvent: deuterated chloroform, standard: CFCl$_3$) δ (ppm): −80.0 (1F), −81.9 (3F), −82.7 (3F), −84.7 to −85.0 (12F), −86.0 (1F), −90.5 to −93.0 (12F), −121.1 (4F), −121.5 (8F), −128.0 (12F), −130.3 (2F), −132.5 (1F), −145.3 (6F).

Ex. 1-4

An autoclave (made of nickel, inner volume: 1 L) was prepared, and at the gas outlet of the autoclave, a condenser maintained at 0° C., a NaF pellets-packed layer and a condenser maintained at −10° C. were set in series. Further, a liquid returning line for returning a condensed liquid from the condenser maintained at −10° C. to the autoclave, was set.

Into the autoclave, 750 g of R-113 (CF$_2$ClCFCl$_2$) was charged and stirred while maintained at 25° C. Into the autoclave, nitrogen gas was blown at 25° C. for one hour, and then, fluorine gas diluted to 20 vol % with nitrogen gas (hereinafter referred to as 20% fluorine gas) was blown at 25° C. for 1 hour at a flow rate of 3.2 L/hr. Then, while blowing the 20% fluorine gas at the same flow rate, a solution prepared by dissolving 130 g of the compound (6-1) in 448 g of R-113, was injected into the autoclave, over 22 hours.

Then, while blowing the 20% fluorine gas at the same flow rate, the autoclave was pressurized to an internal pressure of up to 0.15 MPa (gauge pressure). Into the autoclave, 8 mL of a benzene solution containing 0.015 g/mL of benzene in R-113, was injected while heating from 25° C. to 40° C., whereupon the benzene solution inlet of the autoclave was closed. After stirring for 20 minutes, 4 mL of the benzene solution was injected again while maintaining the temperature at 40° C., whereupon the inlet was closed. The same operation was further repeated seven times. The total amount of benzene injected was 0.6 g.

Further, while blowing the 20% fluorine gas at the same flow rate, stirring was continued for 1 hour. Then, the pressure in the autoclave was made to be the atmospheric pressure, and nitrogen gas was blown in for 1 hour. The content of the autoclave was concentrated by an evaporator to obtain 145 g (yield: 98%) of a compound (7-1) represented by the following formula (7-1).

$$\begin{aligned}&CF_3CF_2CF_2OCF(CF_3)C(O)O-\\&\quad(CF_2CF_2CF_2CF_2OCF_2CF_2O)_3-CF_2CF_2-\\&\quad(OCF_2CF_2OCF_2CF_2CF_2CF_2)_3-OC(O)CF(CF_3)\\&\quad OCF_2CF_2CF_3\end{aligned} \qquad (7\text{-}1)$$

NMR Spectrum of Compound (7-1):
$^{19}$F-NMR (282.7 MHz, solvent: deuterated chloroform, standard: CFCl$_3$) δ (ppm): −80.0 (1F), −82.0 to −82.5 (6F), −84.0 (24F), −87.8 (4F), −89.2 (28F), −126.5 (24F), −130.4 (2F), −132.4 (1F).

Ex. 1-5

Into a 500 mL round-bottomed eggplant flask made of a tetrafluoroethylene-perfluoro(alkoxy vinyl ether) copolymer (PFA), 145 g of the compound (7-1) was put. While cooling in an ice bath and stirring under a nitrogen atmosphere, 35 g of methanol was slowly dropwise added from a dropping funnel. While bubbling with nitrogen, stirring was continued for 12 hours. The reaction mixture was concentrated by an evaporator to obtain 108 g (yield: 100%) of a compound (A5-1) represented by the following formula (A5-1).

$$\begin{aligned}&CH_3OC(O)CF_2CF_2CF_2-O-CF_2CF_2O\\&\quad(CF_2CF_2CF_2OCF_2CF_2O)_2-CF_2CF_2-\\&\quad(OCF_2CF_2OCF_2CF_2CF_2)_2OCF_2CF_2-O-\\&\quad CF_2CF_2CF_2C(O)OCH_3\end{aligned} \qquad (A5\text{-}1)$$

NMR Spectrum of the Compound (A5-1):
$^1$H-NMR (300.4 MHz, solvent: deuterated chloroform, standard: TMS) δ (ppm): 3.9 (6H).
$^{19}$F-NMR (282.7 MHz, solvent: deuterated chloroform, standard: CFCl$_3$) δ (ppm): −84.0 (28F), −89.2 (28F), −119.8 (4F), −126.5 (24F).

Ex. 1-6

Into a 300 mL three-necked round-bottomed flask, 200 g of ethanol, 2.1 g of lithium chloride and 100 g of the compound (A5-1) were put, and while cooling in an ice bath and stirring under a nitrogen atmosphere, a solution having 9.5 g of sodium borohydride powder dissolved in 200 g of ethanol, was dropwise added. After the dropwise addition of the entire amount, the ice bath was removed, and stirring was continued for 12 hours while slowly warming to room temperature. Then, after cooling again in an ice bath, a hydrochloric acid aqueous solution was dropwise added until the liquid became acidic. After completion of the reaction, the reaction solution was washed once with water and once with a saturated sodium chloride aqueous solution, and the organic phase was recovered. The recovered liquid was concentrated by an evaporator. The recovered concentrate was distilled under reduced pressure, and the obtained crude product was purified on a silica gel column by the method disclosed in Examples of JP-A-2009-197210 and then, supercritically purified by the method disclosed in Examples of JP-A-2009-197210, to obtain 95 g (yield: 98%) of a compound (A1-1) represented by the following formula (A1-1). The number average molecular weight of the compound (A1-1) was 2,100, and the molecular weight distribution was 1.05.

$$\begin{aligned}&HOCH_2CF_2CF_2CF_2-O-CF_2CF_2O\\&\quad(CF_2CF_2CF_2CF_2OCF_2CF_2O)_2-CF_2CF_2-\\&\quad(OCF_2CF_2OCF_2CF_2CF_2CF_2)_2OCF_2CF_2-O-\\&\quad CF_2CF_2CF_2CH_2OH\end{aligned} \qquad (A1\text{-}1)$$

NMR Spectrum of Compound (A1-1):
$^1$H-NMR (300.4 MHz, solvent: deuterated chloroform, standard: TMS) δ (ppm): 4.1 (4H).
$^{19}$F-NMR (282.7 MHz, solvent: deuterated chloroform, standard: CFCl$_3$) δ (ppm): −84.0 (28F), −89.2 (28F), −123.3 (4F), −126.5 (24F).

(Production of Article)

The compound (A1-1) was dissolved in Vertrel (registered trademark) XF (manufactured by DuPont) so that the concentration became to be 0.05 mass %, to prepare a liquid composition.

The liquid composition was applied by dip coating on a silicon wafer to obtain an article (a surface layer-attached substrate). That is, using a micro speed dip coater (manufactured by SDI Co., Ltd.) as a dip coater, a silicon wafer was dipped at a rate of 10 mm/sec., immersed for 60 seconds, and then withdrawn at a rate of 2 mm/sec. The withdrawn silicon wafer was heated for 10 minutes in an oven of 150° C. to form a surface layer, to obtain the article.

Ex. 2

Into a 300 mL three-necked round-bottomed flask, 50 g of tert-butyl alcohol, 5.6 g of potassium tert-butoxide and 100 g of the compound (A1-1) before purification (as the crude product) were put, and while heating to 80° C. and stirring under a nitrogen atmosphere, 7.4 g of glycidol (compound (9)) was dropwise added. After the dropwise addition of the entire amount, stirring was continued for 5 hours. Then, after cooling in an ice bath, a hydrochloric acid aqueous solution was dropwise added until the liquid became acidic. After completion of the reaction, the reaction solution was washed once with water and once with a saturated sodium chloride aqueous solution, and the organic phase was recovered. The recovered liquid was concentrated by an evaporator. The recovered concentrate was distilled under reduced pressure and then purified in the same manner as in Ex. 1 to obtain 100 g (yield: 93%) of a compound (A2-1) represented by the following formula (A2-1). The number average molecular weight of the compound (A2-1) was 2,200, and the molecular weight distribution was 1.05. An article was obtained in the same manner as in Ex. 1, except that the compound (A2-1) was used.

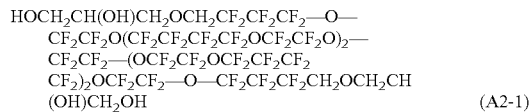
(A2-1)

NMR spectrum of compound (A2-1): $^{1}$H-NMR (300.4 MHz, solvent: deuterated chloroform, standard: TMS) δ (ppm): 3.5 (8H), 3.7 (2H), 3.8 (4H).

$^{19}$F-NMR (282.7 MHz, solvent: deuterated chloroform, standard: CFCl$_3$) δ (ppm): −84.0 (28F), −89.2 (28F), −123.3 (4F), −126.5 (24F).

Ex. 3

A compound (C-1) represented by the following formula (C-1) (manufactured by Solvay, Fomblin (registered trademark) Z DOL4000, number average molecular weight: 4,000) was prepared. An article was obtained in the same manner as in Ex. 1, except that the compound (C-1) was used.

HO—(CF$_2$O)$_s$(CF$_2$CF$_2$O)$_t$—H    (C-1)

Ex. 4

Into a 300 mL three-necked round-bottomed flask, 50 g of tert-butyl alcohol, 2.8 g of potassium tert-butoxide and 100 g of the compound (C-1) were put, and while heating to 80° C. and stirring under a nitrogen atmosphere, 3.7 g of glycidol was dropwise added. After the dropwise addition of the entire amount, stirring was continued for 5 hours. Then, while cooling in an ice bath, a hydrochloric acid aqueous solution was dropwise added until the liquid became acidic. After completion of the reaction, the reaction solution was washed once with water and once with a saturated sodium chloride aqueous solution, and the organic phase was recovered. The recovered liquid was concentrated by an evaporator. The recovered concentrate was distilled under reduced pressure to obtain 99 g (yield: 95%) of a compound (C-2) represented by the following formula (C-2). An article was obtained in the same manner as in Ex. 1 except that the compound (C-2) was used.

HOCH$_2$CH(OH)CH$_2$O—(CF$_2$O)$_s$(CF$_2$CF$_2$O)$_t$—CH$_2$CH(OH)CH$_2$OH    (C-2)

NMR Spectrum of Compound (C-2):
$^{1}$H-NMR (300.4 MHz, solvent: deuterated chloroform, standard: TMS) δ (ppm): 3.5 (8H), 3.7 (2H), 3.8 (4H).

$^{19}$F-NMR (282.7 MHz, solvent: deuterated chloroform, standard: CFCl$_3$) δ (ppm): −84.0 (28F), −89.2 (28F), −123.3 (4F), −126.5 (24F).

[Evaluation]

With respect to the articles in Ex. 1 to 4, the dynamic friction coefficient and F/Si of the outermost surface (where a surface layer is formed on the surface of each article) were measured. Further, with respect to the articles in Ex. 1 to 4, in order to confirm the adhesion between the fluorinated ether compound and the carbon protective film on the substrate, each article was held in a vacuum oven set at 150° C. under 10 mmHg for one week, and the dynamic friction coefficient and F/Si after the treatment, were measured. The results are shown in Table 1.

TABLE 1

|  |  | Ex. 1 | Ex. 2 | Ex. 3 | Ex. 4 |
|---|---|---|---|---|---|
|  | Compound | (A1-1) | (A2-1) | (C-1) | (C-2) |
| Before treatment | Dynamic friction coefficient | ○ | ○ | ○ | ○ |
|  | F/Si | ○ | ○ | X (more than 1.0) | X (more than 1.0) |
| After treatment | Dynamic friction coefficient | X | ○ | X | ○ |
|  | F/Si | X (less than 0.8) | ○ | X (less than 0.8) | X (more than 1.0) |

The value of F/Si represents the amount of the fluorinated polyether attached on the substrate, i.e. the thickness of the surface layer, and from the conventional knowledge, it is known to be suitably at a level of from 0.8 to 1.0 from the viewpoint of lubricity.

Before the treatment, in Ex. 3 and 4, F/Si indicates a high numerical value, that is, it is seen that the surface layer is too thick, and the lubricity is insufficient. On the other hand, in Ex. 1 and 2, F/Si is within the desired range, that is, a suitable surface layer is formed.

After the treatment, in Ex. 1 and 3, F/Si is lower than the desired range, and further, the dynamic friction coefficient shows a high numerical value, i.e. it is indicated that by the treatment, a portion of the surface layer has been lost. On the other hand, in Ex. 2 and 4, there is no change in both the dynamic friction coefficient and F/Si before and after treatment, which shows that the surface layer is firmly adhered to the substrate.

Ex. 5

Ex. 5-1

While a compound (10-1) represented by the following formula (10-1), triethylamine and acetonitrile are stirred, mesyl chloride is added. After confirming by NMR that the compound (10-1) has been consumed, the organic phase is washed with water, and the solvent in the obtained organic phase is distilled off, to obtain a compound (11-1) represented by the following formula (11-1).

HOCH$_2$CF$_3$ (10-1)

CH$_3$SO$_2$—OCH$_2$CF$_3$ (11-1)

Ex. 5-2

In the same manner as in Ex. 1, the compound (A1-1), i.e. a compound (13-1) represented by the following formula (13-1) is obtained. (CF$_2$CF$_2$O) units and (CF$_2$CF$_2$CF$_2$CF$_2$O) units are alternately arranged except for some. The compound (13-1) may be used as a fluorinated polyether compound (B).

HOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$OH (13-1)

Ex. 5-3

In tetrahydrofuran, the compound (13-1) and metallic sodium are sufficiently reacted while cooling in an ice bath, and then, dropwise added to the compound (11-1). After confirming by NMR that the compound (11-1) has been consumed, the organic phase is washed with 0.1 N hydrochloric acid, and the solvent in the obtained organic phase is distilled off, to obtain a mixture of compounds (16-1) and (16-2) represented by the following formulae and the compound (13-1). The compound (16-1) may be used as a fluorinated polyether compound (B).

HOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$OCH$_2$CF$_3$ (16-1)

CF$_3$CH$_2$OCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$OCH$_2$CF$_3$ (16-2)

The mixture is fractionation-purified by silica gel column chromatography to obtain the desired compound (16-1). As the silica gel, D-50-120A, D-75-60A, etc. manufactured by AGC Si-Tech Co., Ltd. may be used. As the developing solvent, as a non-polar solvent, ASAHIKLIN AK-225, ASAHIKLIN AC-2000, ASAHIKLIN AC-6000, etc. manufactured by Asahi Glass Co., Ltd. and as a polar solvent, ASAHIKLIN AE-3000, ethyl acetate, acetone, ethanol, etc. may be used. The silica gel is used in an amount of from 5 to 20 times by mass relative to ones to be fractionated. The developing solvent is used in an amount of from 20 to 100 times by volume to ones to be fractionated. Among the fractionated ones, the abundance ratios of the compounds (16-1) and (16-2) and the compound (13-1) are judged by a method such as NMR, HPLC, etc.

Ex. 5-4

In tetrahydrofuran, the compound (13-1) and metallic sodium are sufficiently reacted and then, a compound (12-1) represented by the following formula (12-1) is dropwise added. A mixture of compounds (15-1) and (15-2) and the compound (13-1) is obtained. Here, Ph is a phenyl group. The compounds (15-1) and (15-2) each may be used as a fluorinated polyether compound (B).

Ph-I (12-1)

PhOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$OH (15-1)

PhOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$OPh (15-2)

The mixture is fractionation-purified by silica gel column chromatography to obtain the compound (15-1). As the silica gel, D-50-120A, D-75-60A, etc. manufactured by AGC Si-Tech Co., Ltd. may be used. As the developing solvent, as a non-polar solvent, ASAHIKLIN AK-225, ASAHIKLIN AC-2000, ASAHIKLIN AC-6000, etc. manufactured by Asahi Glass Co., Ltd., and as a polar solvent, ASAHIKLIN AE-3000 ethyl acetate, acetone, ethanol, etc. may be used. The silica gel is used in an amount of from 5 to 20 times by mass relative to ones to be fractionated. The developing solvent is used in an amount of from 20 to 100 times by volume to ones to be fractionated. Among the fractionated ones, the abundance ratios of the compounds (15-1) and (15-2) and the compound (13-1) are judged by a method such as NMR, HPLC, etc.

Ex. 5-5

While the compound (3-1), triethylamine and acetonitrile are stirred, mesyl chloride is added. After confirming by NMR that the compound (3-1) has been consumed, the organic phase is washed with water, and the solvent in the obtained organic phase is distilled off, to obtain a compound (18-1) represented by the following formula (18-1).

HO—CH$_2$CH$_2$—OH (3-1)

CH$_3$SO$_2$—O—CH$_2$CH$_2$—O—SO$_2$CH$_3$ (18-1)

Ex. 5-6

In tetrahydrofuran, the compound (15-1) and metallic sodium are sufficiently reacted, and then, the compound (18-1) is dropwise added. After confirming by NMR that the compound (18-1) has been consumed, the organic phase is washed with 0.1N hydrochloric acid, and the solvent in the obtained organic phase is distilled off, to obtain a mixture of compounds (19-1) and (A61-1) represented by the following formulae and the compound (18-1).

PhOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$O—CH$_2$CH$_2$—O—SO$_2$CH$_3$ (19-1)

PhOCH$_2$CF$_2$CF$_2$CF$_2$—O—[(CF$_2$CF$_2$O)$_7$—(CF$_2$CF$_2$CF$_2$CF$_2$O)$_4$]—CF$_2$CF$_2$CF$_2$CH$_2$O—CH$_2$CH$_2$—OCH$_2$CF$_2$CF$_2$CF$_2$—[(OCF$_2$CF$_2$)$_7$—(OCF$_2$CF$_2$CF$_2$CF$_2$)$_4$]—O—CF$_2$CF$_2$CF$_2$CH$_2$OPh (A61-1)

The mixture is fractionation-purified by silica gel column chromatography to obtain the desired compounds (19-1) and (A61-1). As the silica gel, D-50-120A, D-75-60A, etc. manufactured by AGC Si-Tech Co., Ltd. may be used. As the developing solvent, as a non-polar solvent, ASAHIKLIN AK-225, ASAHIKLIN AC-2000, ASAHIKLIN AC-6000 manufactured by Asahi Glass Co., Ltd. and as the polar solvent, ASAHIKLIN AE-3000, ethyl acetate, acetone, ethanol, etc. may be used. The silica gel is used in an amount of from 5 to 20 times by mass relative to ones to be fractionated. The developing solvent is used in an amount of from 20 to 100 times by volume to ones to be fractionated. Among the fractionated ones, the abundance ratios of the compounds (19-1) and (A61-1) and the compound (18-1) are judged by a method such as NMR, HPLC, etc.

Ex. 5-7

In tetrahydrofuran, the compound (16-1) and metallic sodium are sufficiently reacted and then, the compound (19-1) is dropwise added. A compound (A62-1) represented by the following formula (A62-1) is obtained.

$$\text{PhOCH}_2\text{CF}_2\text{CF}_2\text{CF}_2\text{—O—[(CF}_2\text{CF}_2\text{O})_7\text{—} \\ (\text{CF}_2\text{CF}_2\text{CF}_2\text{CF}_2\text{O})_4]\text{—CF}_2\text{CF}_2\text{CF}_2\text{CH}_2\text{O—} \\ \text{CH}_2\text{CH}_2\text{—OCH}_2\text{CF}_2\text{CF}_2\text{CF}_2\text{—[(OCF}_2\text{CF}_2)_7\text{—} \\ (\text{OCF}_2\text{CF}_2\text{CF}_2\text{CF}_2)_4]\text{—O—} \\ \text{CF}_2\text{CF}_2\text{CF}_2\text{CH}_2\text{OCH}_2\text{CF}_3 \quad (\text{A62-1})$$

Ex. 6

Ex. 6-1

A reflux condenser is attached to a 300 mL three-necked flask; 0.3 mol of the compound (15-1), 0.33 mol of metallic sodium and 100 mL of dehydrated tetrahydrofuran are added, and stirring is continued at 70° C. until the metallic sodium is consumed. After the metallic sodium is consumed, 0.1 mol of a cyclo trimmer of phosphonitrile chloride is added and similarly reacted at 70° C., and upon confirming consumption of the compound (15-1) by NMR, the reaction is terminated. After completion of the reaction, 50 g of ASAHIKLIN AK-225 (manufactured by Asahi Glass Co., Ltd.) and 50 g of 0.1 N hydrochloric acid are added and thoroughly stirred, and then, only the organic phase is taken out. Again, 50 g of 0.1 N hydrochloric acid is added, and the organic phase is washed, whereupon the organic phase is taken out, and the solvent is distilled off, to obtain a mixture of compounds (20-1) represented by the following formula (20-1).

$$\{\text{PhOCH}_2\text{CF}_2\text{CF}_2\text{CF}_2\text{—O—[(CF}_2\text{CF}_2\text{O})_7\text{—} \\ (\text{CF}_2\text{CF}_2\text{CF}_2\text{CF}_2\text{O})_4]\text{—CF}_2\text{CF}_2\text{CF}_2\text{CH}_2\text{O}\}_{m1}\text{—} \\ \text{P}_3\text{N}_3\text{—(Cl)}_{n1} \quad (20\text{-}1)$$

Ex. 6-2

A reflux condenser is attached to a 300 mL three-necked flask; 0.3 mol of the compound (16-1) and 0.33 mol of metallic sodium and 100 mL of dehydrated tetrahydrofuran are added, and stirring is continued at 70° C. until the metallic sodium is consumed. After the metallic sodium is consumed, the mixture of compounds (20-1) is added and similarly reacted at 70° C., and upon confirming consumption of compounds (20-1) by NMR, the reaction is terminated. After completion of the reaction, 50 g of ASAHIKLIN AK-225 (manufactured by Asahi Glass Co., Ltd.) and 50 g of 0.1 N hydrochloric acid are added and thoroughly stirred, and then, only the organic phase is taken out. Again, 50 g of 0.1 N hydrochloric acid is added, and the organic phase is washed, whereupon the organic phase is taken out, and the solvent is distilled off to obtain a mixture of compounds (A63-1) represented by the following formula (A63-1).

$$\{\text{PhOCH}_2\text{CF}_2\text{CF}_2\text{CF}_2\text{—O—[(CF}_2\text{CF}_2\text{O})_7\text{—} \\ (\text{CF}_2\text{CF}_2\text{CF}_2\text{CF}_2\text{O})_4]\text{—CF}_2\text{CF}_2\text{CF}_2\text{CH}_2\text{O}\}_{m1}\text{—} \\ \text{P}_3\text{N}_3\text{—}\{\text{OCH}_2\text{CF}_2\text{CF}_2\text{CF}_2\text{—[(OCF}_2\text{CF}_2)_7\text{—} \\ (\text{OCF}_2\text{CF}_2\text{CF}_2\text{CF}_2)_4]\text{O—} \\ \text{CF}_2\text{CF}_2\text{CF}_2\text{CH}_2\text{OCH}_2\text{CF}_3\}_{n1} \quad (\text{A63-1})$$

Ex. 7

Ex. 7-1

To a compound (21-1) represented by the following formula (21-1) (manufactured by NOF CORPORATION, Polyserine (registered trademark) DC-1100, ($CF_2CF_2O$) units and ($CF_2CF_2CF_2CF_2O$) units are randomly arranged), sodium fluoride is added and thoroughly stirred, and a compound (5-2) represented by the following formula (5-2) is dropwise added and then, sufficiently reacted at room temperature. After confirming by NMR that the compound (21-1) is consumed, sodium fluoride is removed by a press filter, and an excess compound (5-2) is distilled off under reduced pressure, to obtain a compound (22-1) represented by the following formula (22-1).

$$\text{HO—[(CH}_2\text{CH}_2\text{O})_{15}\text{—(CH}_2\text{CH}_2\text{CH}_2\text{CH}_2\text{O})_5]\text{—H} \quad (21\text{-}1)$$

$$\text{CF}_3\text{CF}_2\text{CF}_2\text{OCF(CF}_3)\text{CF}_2\text{OCF(CF}_3)\text{C(O)F} \quad (5\text{-}2)$$

$$\text{CF}_3\text{CF}_2\text{CF}_2\text{OCF(CF}_3)\text{CF}_2\text{OCF(CF}_3)\text{C(O)O—} \\ [(\text{CH}_2\text{CH}_2\text{O})_{15}\text{—(CH}_2\text{CH}_2\text{CH}_2\text{CH}_2\text{O})_5]\text{—C(O)} \\ \text{CF(CF}_3)\text{OCF}_2(\text{CF}_3)\text{CFOCF}_2\text{CF}_2\text{CF}_3 \quad (22\text{-}1)$$

Ex. 7-2

Into the autoclave (made of nickel), R-113 ($CF_2ClCFCl_2$) is introduced, then nitrogen gas is blown in at 25° C. for one hour, and then, 20% fluorine gas is blown in at 25° C. for one hour. While 20% fluorine gas is blown at the same flow rate, the compound (22-1) diluted by R-113 is continuously fed. When the feeding is complete, the internal pressure is raised to 0.15 MPa (gauge pressure), and the temperature is raised from 25° C. to 40° C. with stirring. After confirming by NMR that no hydrogen atoms remain, nitrogen gas is blown in at 25° C. for one hour to terminate the reaction. The solvent is distilled off from the obtained reaction solution to obtain a compound (23-1) represented by the following formula (23-1).

$$\text{CF}_3\text{CF}_2\text{CF}_2\text{OCF(CF}_3)\text{CF}_2\text{OCF(CF}_3)\text{C(O)O—} \\ [(\text{CF}_2\text{CF}_2\text{O})_{15}\text{—(CF}_2\text{CF}_2\text{CF}_2\text{CF}_2\text{O})_5]\text{—C(O)CF} \\ (\text{CF}_3)\text{OCF}_2(\text{CF}_3)\text{CFOCF}_2\text{CF}_2\text{CF}_3 \quad (23\text{-}1)$$

Ex. 7-3

The compound (23-1) is stirred while cooling in an ice bath, and under a nitrogen atmosphere, methanol is slowly dropwise added, followed by stirring for 12 hours while bubbling with nitrogen. After confirming the consumption of the compound (23-1) by NMR, the solvent is distilled off from the reaction solution to obtain a mixture of compounds (24-1i) to (24-1iii) represented by the following formulae. The compounds (24-1i) to (24-1iii) each may be used as a fluorinated polyether compound (B).

$$\text{CH}_3\text{OC(O)CF}_2\text{CF}_2\text{CF}_2\text{—O—[(CF}_2\text{CF}_2\text{O})_{15}\text{—} \\ (\text{CF}_2\text{CF}_2\text{CF}_2\text{CF}_2\text{O})_3]\text{—CF}_2\text{CF}_2\text{CF}_2\text{C(O)OCH}_3 \quad (24\text{-}1\text{i})$$

$$\text{CH}_3\text{OC(O)CF}_2\text{—O—[(CF}_2\text{CF}_2\text{O})_{14}\text{—} \\ (\text{CF}_2\text{CF}_2\text{CF}_2\text{CF}_2\text{O})_4]\text{—CF}_2\text{CF}_2\text{CF}_2\text{C(O)OCH}_3 \quad (24\text{-}1\text{ii})$$

$$\text{CH}_3\text{OC(O)CF}_2\text{—O—[(CF}_2\text{CF}_2\text{O})_{13}\text{—} \\ (\text{CF}_2\text{CF}_2\text{CF}_2\text{CF}_2\text{O})_5]\text{—CF}_2\text{C(O)OCH}_3 \quad (24\text{-}1\text{iii})$$

Ex. 7-4

In a reactor, ethanol, lithium chloride, and the mixture of compounds (24-1i) to (24-1iii) are put and stirred while cooling in an ice bath, and under a nitrogen atmosphere, a dispersion having a sodium borohydride powder dispersed in ethanol is dropwise added. After the dropwise addition of the entire amount, stirring is continued while slowly warmed to room temperature. After confirming by NMR that compounds (24-1i) to (24-1iii) have been consumed, the reaction solution is again cooled in an ice bath, and 0.1 N hydrochloric acid and ASAHIKLIN AK-225 are added until the liquid becomes acidic, whereupon the organic phase is recovered. After washing again twice with water, the organic phase is recovered. The solvent is distilled off from the recovered organic phase, to obtain a mixture of compounds (13a-1i) to (13a-1iii). The compounds (13a-1i) to (13a-1iii) each may be used as a fluorinated polyether compound (B).

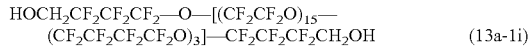  (13a-1i)

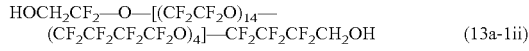  (13a-1ii)

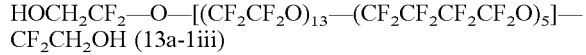  (13a-1iii)

Ex. 8

Ex. 8-1

A compound (25-1) represented by the following formula (25-1) (manufactured by NOF CORPORATION, PEG#200) and a compound (26-1) represented by the following formula (26-1) (manufactured by NOF CORPORATION, Uniol (registered trademark) PB-500) are prepared.

$$HO-(CH_2CH_2O)_4-H \quad (25\text{-}1)$$

$$HO-(CH_2CH_2CH_2CH_2O)_7-H \quad (26\text{-}1)$$

While the compound (25-1) or compound (26-1), triethylamine and acetonitrile are stirred, at least two equivalents of mesyl chloride is added. After confirming by NMR that the compound (25-1) or compound (26-1) has been consumed, the organic phase is washed with water, and the solvent in the obtained organic phase is distilled off, to obtain a compound (27-1) represented by the formula (27-1) or a compound (28-1) represented by the following formula (28-1).

$$CH_3SO_2-O-(CH_2CH_2O)_4-SO_2CH_3 \quad (27\text{-}1)$$

$$CH_3SO_2-O-(CH_2CH_2CH_2CH_2O)_7-SO_2CH_3 \quad (28\text{-}1)$$

Ex. 8-2

In tetrahydrofuran, the compound (26-1) and metallic sodium are sufficiently reacted while cooling in an ice bath, and then, the compound (27-1) is dropwise added. Or, in tetrahydrofuran, the compound (25-1) and metallic sodium are sufficiently reacted while cooling in an ice bath, and then, the compound (28-1) is dropwise added. At that time, an alkoxide of the compound (26-1) or compound (25-1) is preferably present in large excess to the compound (27-1) or compound (28-1) to be dropwise added, and the dropping rate of the compound (27-1) or compound (28-1) is preferably sufficiently slow to the reaction. After confirming by NMR that the compound (27-1) or compound (28-1) has been consumed, the organic phase is washed with 0.1 N hydrochloric acid, and the solvent in the obtained organic phase is distilled off, to obtain a compound (29-1i) represented by the following formula (29-1i) or a compound (29-1ii) represented by the following formula (29-1ii).

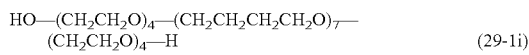  (29-1i)

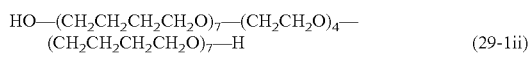  (29-1ii)

Ex. 8-3

To the compound (29-1i) or compound (29-1ii), sodium fluoride is added and thoroughly stirred, and the compound (5-2) is dropwise added and then sufficiently reacted at room temperature. After confirming by NMR that the compound (29-1i) or compound (29-1ii) has been consumed, sodium fluoride is removed by a press filter, and an excess compound (5-2) is distilled off under reduced pressure, to obtain a compound (30-1i) represented by the following formula (30-1i) or a compound (30-1ii) represented by the following formula (30-1ii).

$$CF_3CF_2CF_2OCF(CF_3)CF_2OCF(CF_3)C(O)F \quad (5\text{-}2)$$

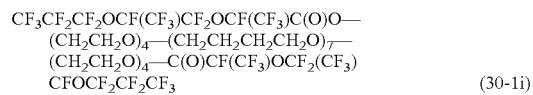  (30-1i)

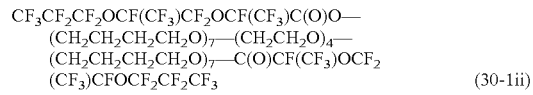  (30-1ii)

Ex. 8-4

Into an autoclave (made of nickel), R-113 ($CF_2ClCFCl_2$) was introduced; nitrogen gas was blown in at 25° C. for one hour and then, 20% fluorine gas is blown in at 25° C. for one hour. While blowing 20% fluorine gas at the same flow rate, the compound (30-1i) or compound (30-1ii) diluted by R-113 is continuously fed. When the feeding is completed, the internal pressure is raised to 0.15 MPa (gauge pressure), and stirring is conducted while the temperature is raised from 25° C. to 40° C. After confirming by NMR that no hydrogen atoms remain, nitrogen gas is blown in at 25° C. for one hour to terminate the reaction. The solvent is distilled off from the obtained reaction solution, to obtain a compound (31-1i) represented by the following formula (31-1i) or a compound (31-1ii) represented by the following formula (31-1ii).

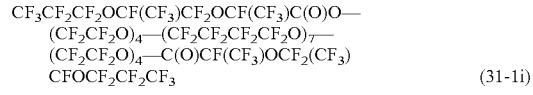  (31-1i)

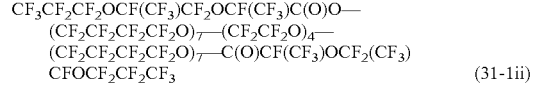  (31-1ii)

Ex. 8-5

The compound (31-1i) or compound (31-1ii) is stirred while cooling in an ice bath; under a nitrogen atmosphere, methanol is slowly dropwise added and then stirred for 12 hours while bubbling with nitrogen. After confirming consumption of the compound (31-1i) or compound (31-1ii) by NMR, the solvent is distilled off from the reaction solution, to obtain a compound (32-1i) represented by the following formula (32-1i) or a compound (32-1ii) represented by the following formula (32-1ii). The compound (32-1i) or (32-1ii) may be used as a fluorinated polyether compound (B).

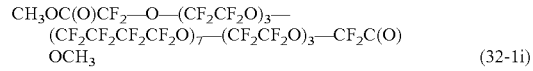  (32-1i)

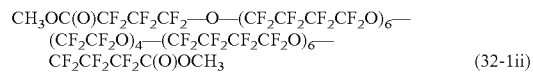  (32-1ii)

Ex. 8-6

In a reactor, ethanol, lithium chloride, and the compound (32-1i) or compound (32-1ii), are put and stirred while cooling in an ice bath, and under nitrogen atmosphere, a dispersion having sodium borohydride powder dispersed in ethanol is dropwise added. After the dropwise addition of the entire amount, stirring is continued while slowly raising the temperature to room temperature. After confirming by NMR that the compound (32-1i) or compound (32-1ii) has been consumed, the reaction solution is again cooled in an ice bath, and 0.1 N hydrochloric acid and ASAHIKLIN AK-225 are added until the liquid becomes acidic, whereupon the organic phase is recovered. After washing again twice with water, the organic phase is recovered. The solvent is distilled off from the obtained organic layer, to obtain a compound (13b-1i) represented by the following formula (13b-1i) or a compound (13b-1ii) represented by the following formula (13b-1ii). The compound (13b-1i) or (13b-1ii) may be used as a fluorinated polyether compound (B).

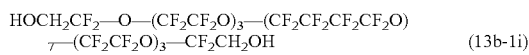

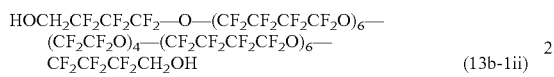  (13b-1ii)

INDUSTRIAL APPLICABILITY

The fluorinated polyether compound of the present invention is useful as a surface modifier (lubricant, etc.) or a surfactant, and is particularly useful as a lubricant to be applied on a diamond-like carbon protective film (DLC film) of a magnetic disk to impart lubricity.

This application is a continuation of PCT Application No. PCT/JP2014/070498, filed on Aug. 4, 2014, which is based upon and claims the benefit of priority from Japanese Patent Application No. 2013-168103 filed on Aug. 13, 2013. The contents of those applications are incorporated herein by reference in their entireties.

What is claimed is:

1. A fluorinated polyether compound represented by the following formula (A):

wherein X is a group having a hydroxy group, a carboxy group, an ester group or an aryl group, Y is an (m+n) valent linking group having no etheric oxygen atom at its terminals, Z is a group not having a hydroxy group, a carboxy group, an ester group or an aryl group, and having a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms, m is an integer of from 1 to 10, n is an integer from 0 to 10, m+n is an integer of from 2 to 20, and a, b, c and d are each independently an integer of from 1 to 100, provided that the linking order of a number of $(CF_2CF_2O)$ units and b number of $(CF_2CF_2CF_2CF_2O)$ units in $[(CF_2CF_2O)_a-(CF_2CF_2CF_2CF_2O)_b]$, and the linking order of c number of $(OCF_2CF_2)$ units and d number of $(OCF_2CF_2CF_2CF_2)$ units in $[(OCF_2CF_2)_c-(OCF_2CF_2CF_2CF_2)_d]$, are not limited.

2. The fluorinated polyether compound according to claim 1, which has a number average molecular weight of from 500 to 50,000.

3. The fluorinated polyether compound according to claim 1, wherein b/(a+b) is from 0.2 to 0.8, and d/(c+d) is from 0.2 to 0.8.

4. The fluorinated polyether compound according to claim 1, which has a structure wherein $(OCF_2CF_2)$ units and $(OCF_2CF_2CF_2CF_2)$ units are alternately arranged.

5. The fluorinated polyether compound according to claim 1, wherein X is a $HOCH_2CH(OH)CH_2OCH_2CF_2CF_2CF_2-$ group or a $HOCH_2CH(OH)CH_2OCH_2CF_2-$ group.

6. A fluorinated polyether compound represented by the following formula (B):

wherein X is a group having a hydroxy group, a carboxy group, an ester group or an aryl group, W is a group having a hydroxy group, a carboxy group, an ester group, an aryl group, or a haloalkyl group (provided that the halogen atom is a fluorine atom or a chlorine atom) or a haloalkyl group (provided that the halogen atom is a fluorine atom or a chlorine atom) having an etheric oxygen atom inserted between carbon-carbon atoms, and g and h are each independently an integer of from 1 to 200, provided that the linking order of g number of $(CF_2CF_2O)$ units and h number of $(CF_2CF_2CF_2CF_2O)$ units in $[(CF_2CF_2O)_g-(CF_2CF_2CF_2CF_2O)_h]$ is not limited.

7. The fluorinated polyether compound according to claim 6, which has a number average molecular weight of from 500 to 50,000.

8. The fluorinated polyether compound according to claim 6, wherein h/(g+h) is from 0.2 to 0.8.

9. The fluorinated polyether compound according to claim 6, which has a structure wherein $(CF_2CF_2O)$ units and $(CF_2CF_2CF_2CF_2O)$ units are alternately arranged.

10. The fluorinated polyether compound according to claim 6, wherein X is a $HOCH_2CH(OH)CH_2OCH_2CF_2CF_2CF_2-$ group or a $HOCH_2CH(OH)CH_2OCH_2CF_2-$ group.

11. A lubricant comprising the fluorinated polyether compound as defined in claim 1.

12. A lubricant comprising the fluorinated polyether compound as defined in claim 6.

13. A liquid composition comprising the fluorinated polyether compound as defined in claim 1 and a liquid medium.

14. A liquid composition comprising the fluorinated polyether compound as defined in claim 6 and a liquid medium.

15. An article comprising a substrate and, formed thereon, a film containing the fluorinated polyether compound as defined in claim 1.

16. An article comprising a substrate and, formed thereon, a film containing the fluorinated polyether compound as defined in claim 6.

* * * * *